(12) United States Patent
Sharifi et al.

(10) Patent No.: US 10,265,329 B2
(45) Date of Patent: Apr. 23, 2019

(54) ALTERING STEROID METABOLISM FOR TREATMENT OF STEROID-DEPENDENT DISEASE

(71) Applicants: THE CLEVELAND CLINIC FOUNDATION, Cleveland, OH (US); THE REGENTS OF THE UNIVERSITY OF MICHIGAN, Ann Arbor, MI (US)

(72) Inventors: Nima Sharifi, Cleveland, OH (US); Zhenfei Li, Cleveland, OH (US); Richard Auchus, Cleveland, OH (US)

(73) Assignees: THE CLEVELAND CLINIC FOUNDATION, Cleveland, OH (US); THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 8 days.

(21) Appl. No.: 15/062,740

(22) Filed: Mar. 7, 2016

(65) Prior Publication Data

US 2016/0310509 A1    Oct. 27, 2016

Related U.S. Application Data

(60) Provisional application No. 62/129,215, filed on Mar. 6, 2015, provisional application No. 62/207,594, filed on Aug. 20, 2015.

(51) Int. Cl.
| | |
|---|---|
| *A61K 31/58* | (2006.01) |
| *A61K 45/06* | (2006.01) |
| *A61K 31/473* | (2006.01) |
| *A61K 9/00* | (2006.01) |
| *A61K 31/4166* | (2006.01) |

(52) U.S. Cl.
CPC ............ *A61K 31/58* (2013.01); *A61K 9/0053* (2013.01); *A61K 31/4166* (2013.01); *A61K 31/473* (2013.01); *A61K 45/06* (2013.01)

(58) Field of Classification Search
CPC ....................................................... A61K 31/56
USPC ........................................................ 514/171
See application file for complete search history.

(56) References Cited

PUBLICATIONS

Tay et al., Annals of Oncology, 2004;15:974-978.*
Attard et al., Journal of Clinical Oncology, 2009;27(23):3742-3748.*
Attard, Gerhardt, et al. "Phase I clinical trial of a selective inhibitor of CYP17, abiraterone acetate, confirms that castration-resistant prostate cancer commonly remains hormone driven." Journal of clinical oncology 26.28 (2008): 4563-4571.
Attard, Gerhardt, et al. "Clinical and biochemical consequences of CYP17A1 inhibition with abiraterone given with and without exogenous glucocorticoids in castrate men with advanced prostate cancer." The Journal of Clinical Endocrinology & Metabolism 97.2 (2011): 507-516.
Beer, Tomasz M., et al. "Enzalutamide in metastatic prostate cancer before chemotherapy." New England Journal of Medicine 371.5 (2014): 424-433.

(Continued)

*Primary Examiner* — San Ming R Hui
(74) *Attorney, Agent, or Firm* — Tarolli, Sundheim, Covell & Tummino LLP

(57) ABSTRACT

A method of treating steroid-dependent disease such as prostate cancer in a subject is described that includes administering a therapeutically effective amount a CYP17A inhibitor and an effective amount of a 5-α-reductase inhibitor to the subject.

12 Claims, 10 Drawing Sheets

(56) References Cited

PUBLICATIONS

Biswas, Michael G., and David W. Russell. "Expression cloning and characterization of oxidative 17β-and 3α-hydroxysteroid dehydrogenases from rat and human prostate." Journal of Biological Chemistry 272.25 (1997): 15959-15966.

Byrne, G. C., Y. S. Perry, and J. S. D. Winter. "Steroid Inhibitory Effects upon Human Adrenal 3βHydroxysteroid Dehydrogenase Activity." The Journal of Clinical Endocrinology & Metabolism 62.2 (1986): 413-418.

Carreira, Suzanne, et al. "Tumor clone dynamics in lethal prostate cancer." Science translational medicine 6.254 (2014): 254ra125-254ra125.

Chang, Kai-Hsiung, et al. "A gain-of-function mutation in DHT synthesis in castration-resistant prostate cancer." Cell 154.5 (2013): 1074-1084.

Chang, Kai-Hsiung, et al. "Dihydrotestosterone synthesis bypasses testosterone to drive castration-resistant prostate cancer." Proceedings of the National Academy of Sciences 108.33 (2011): 13728-13733.

Clark, Richard V., et al. "Marked suppression of dihydrotestosterone in men with benign prostatic hyperplasia by dutasteride, a dual 5α-reductase inhibitor." The Journal of Clinical Endocrinology & Metabolism 89.5 (2004): 2179-2184.

Debono, Johann S., et al. "Abiraterone and increased survival in metastatic prostate cancer." New England Journal of Medicine 364.21 (2011): 1995-2005.

Drury, Jason E., et al. "Inhibition of human steroid 5β-reductase (AKR1D1) by finasteride and structure of the enzyme-inhibitor complex." Journal of Biological Chemistry 284.30 (2009): 19786-19790.

Efstathiou, Eleni, et al. "Enzalutamide (ENZA) in combination with abiraterone acetate (AA) in bone metastatic castration resistant prostate cancer (mCRPC)." ASCO Annual Meeting Proceedings. vol. 32. No. 15_suppl. 2014.

Emamekhoo, Hamid, Zhenfei Li, and Nima Sharifi. "Clinical significance of D4A in prostate cancer therapy with abiraterone." Cell Cycle 14.20 (2015): 3213-3214.

Ferraldeschi, Roberta, et al. "Molecular pathways: inhibiting steroid biosynthesis in prostate cancer." Clinical Cancer Research 19.13 (2013): 3353-3359.

Fizazi, Karim, et al. "Phase III, randomized, double-blind, multicenter trial comparing orteronel (TAK-700) plus prednisone with placebo plus prednisone in patients with metastatic castration-resistant prostate cancer that has progressed during or after docetaxel-based therapy: ELM-PC 5." Journal of Clinical Oncology 33.7 (2015): 723-731.

Garrido, Mariana, et al. "A-ring modified steroidal azoles retaining similar potent and slowly reversible CYP17A1 inhibition as abiraterone." The Journal of steroid biochemistry and molecular biology 143 (2014): 1-10.

Gomez, Lissette, Jason R. Kovac, and Dolores J. Lamb. "CYP17A1 inhibitors in castration-resistant prostate cancer." Steroids 95 (2015): 80-87.

Hirsch, Kenneth S., et al. "LY191704: a selective, nonsteroidal inhibitor of human steroid 5 alpha-reductase type 1." Proceedings of the National Academy of Sciences 90.11 (1993): 5277-5281.

Hodgson, Myles C., et al. "The androgen receptor recruits nuclear receptor CoRepressor (N-CoR) in the presence of mifepristone via its N and C termini revealing a novel molecular mechanism for androgen receptor antagonists." Journal of Biological Chemistry 280.8 (2005): 6511-6519.

Knudsen, Karen E., and Trevor M. Penning. "Partners in crime: deregulation of AR activity and androgen synthesis in prostate cancer." Trends in Endocrinology & Metabolism 21.5 (2010): 315-324.

Li, Zhenfei, et al. "Conversion of abiraterone to D4A drives anti-tumour activity in prostate cancer." Nature 523.7560 (2015): 347-351.

Li, Rui, et al. "Abiraterone inhibits 3β-hydroxysteroid dehydrogenase: a rationale for increasing drug exposure in castration-resistant prostate cancer." Clinical cancer research 18.13 (2012): 3571-3579.

Mohler, James L., et al. "Activation of the androgen receptor by intratumoral bioconversion of androstanediol to dihydrotestosterone in prostate cancer." Cancer research 71.4 (2011): 1486-1496.

Mostaghel, Elahe A., et al. "Resistance to CYP17A1 inhibition with abiraterone in castration-resistant prostate cancer: induction of steroidogenesis and androgen receptor splice variants." Clinical cancer research 17.18 (2011): 5913-5925.

Pham, Steven, et al. "Next-generation steroidogenesis inhibitors, dutasteride and abiraterone, attenuate but still do not eliminate androgen biosynthesis in 22RV1 cells in vitro." The Journal of steroid biochemistry and molecular biology 144 (2014): 436-444.

Pienta, Kenneth "A phase II neoadjuvant study of enzalutamide, abiraterone acetate, dutasteride and degarelix in men with localized prostate cancer pre-prostatectomy", clinicaltrials.gov A service of the U.S. National Institutes of Health, Jan. 2015, pp. 1-4.

Richards, Juliet, et al. "Interactions of abiraterone, eplerenone, and prednisolone with wild-type and mutant androgen receptor: a rationale for increasing abiraterone exposure or combining with MDV3100." Cancer research 72.9 (2012): 2176-2182.

Rizner, Tea Lanišnik, et al. "Human type 3 3α-hydroxysteroid dehydrogenase (aldo-keto reductase 1C2) and androgen metabolism in prostate cells." Endocrinology 144.7 (2003): 2922-2932.

Robinson, Dan, et al. "Integrative clinical genomics of advanced prostate cancer." Cell 161.5 (2015): 1215-1228.

Ryan, Charles J. et al, "Randomized Phase 3 Trial of Abiraterone Acetate in Men with Metastatic Castration-Resistant Prostate Cancer and No Prior Chemotherapy", N Engl J Med. Jan. 10, 2013; 368(2): 138-148. doi:10.1056/NEJMoa1209096.

Taplin, Mary-Ellen, "Abiraterone acetate combined with dutasteride for metastatic castrate resistant prostate cancer", clinicaltrials.gov A service of the U.S. National Institutes of Health, Mar. 2016, pp. 1-4.

PCT International Search Report and Written Opinion for PCT/US2016/021181, dated May 25, 2016, pp. 1-13.

ClinicalTrials.gov archive 'View of NCT01393730 on Jul. 12, 2011' (retrieved from internet on Mar. 9, 2018) URL: https://clinicaltrials.gov/archive/NCT01393730/2011_07_12.

ClinicalTrials.gov archive 'View of NCT02159690 on Jun. 9, 2014' (retrieved from internet on Mar. 9, 2018) URL: https://clinicaltrials.gov/archive/NCT02159690/2014_06_09.

Australian Examination Report for corresponding Australian Patent Application No. 2016229991, dated Mar. 13, 2018, pp. 1-4.

* cited by examiner

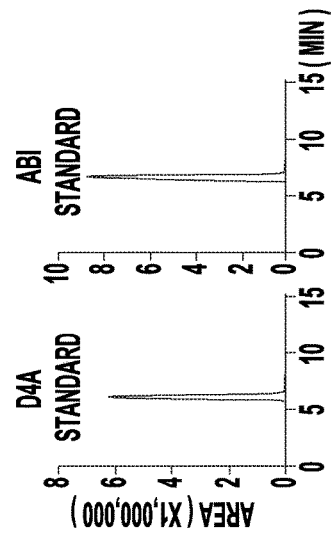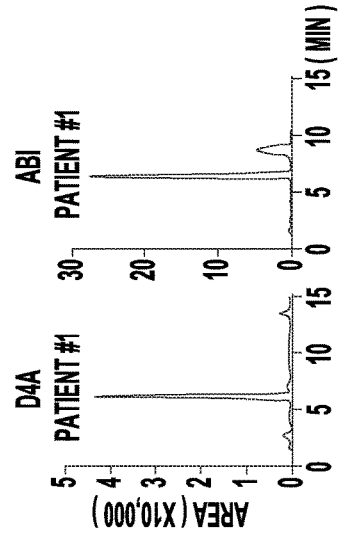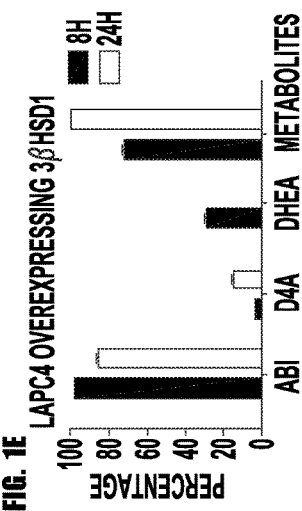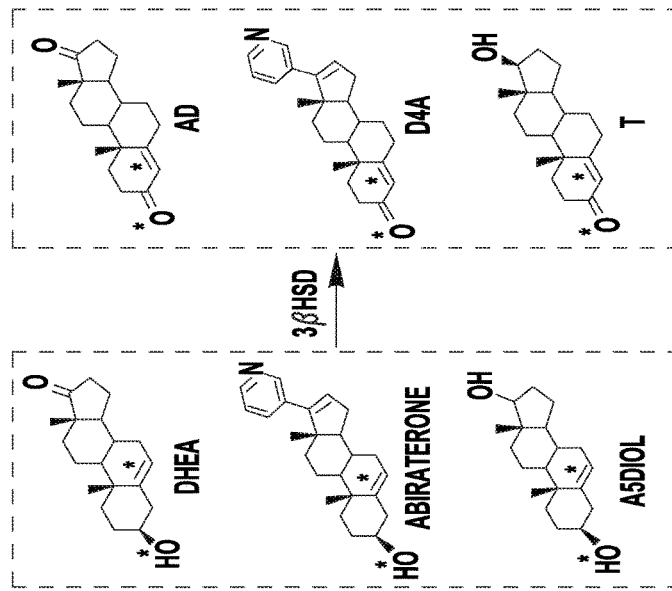
FIG. 1A
FIG. 1B
FIG. 1C
FIG. 1D
FIG. 1E

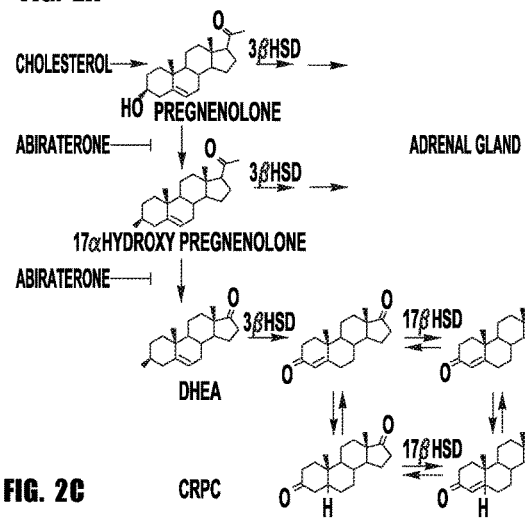
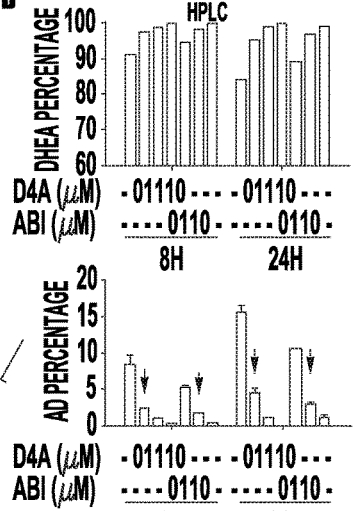
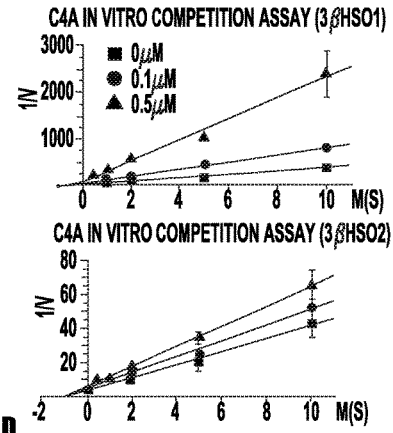
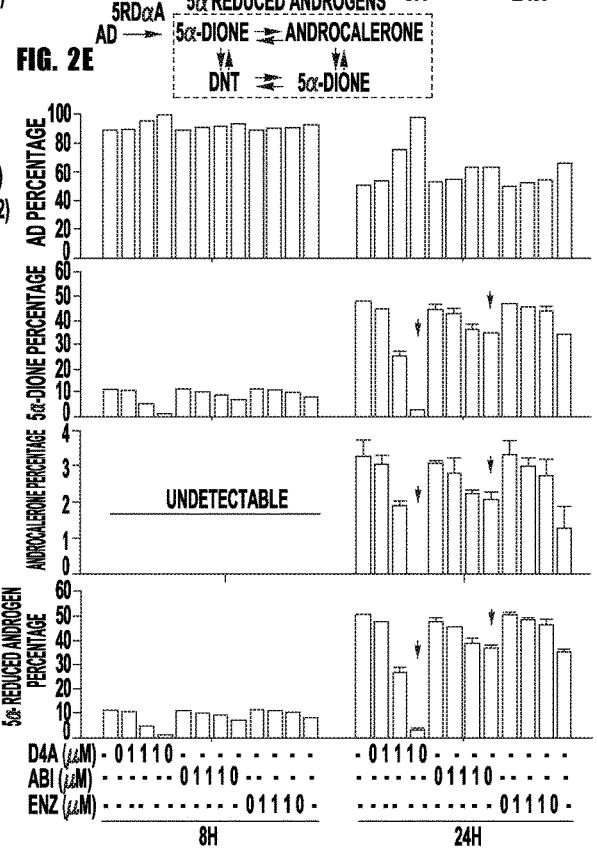
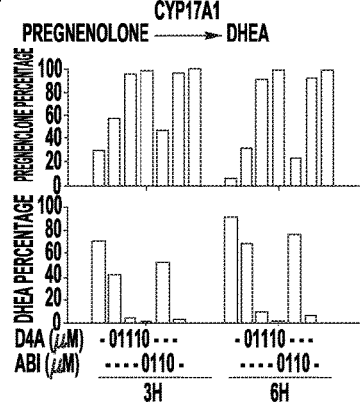

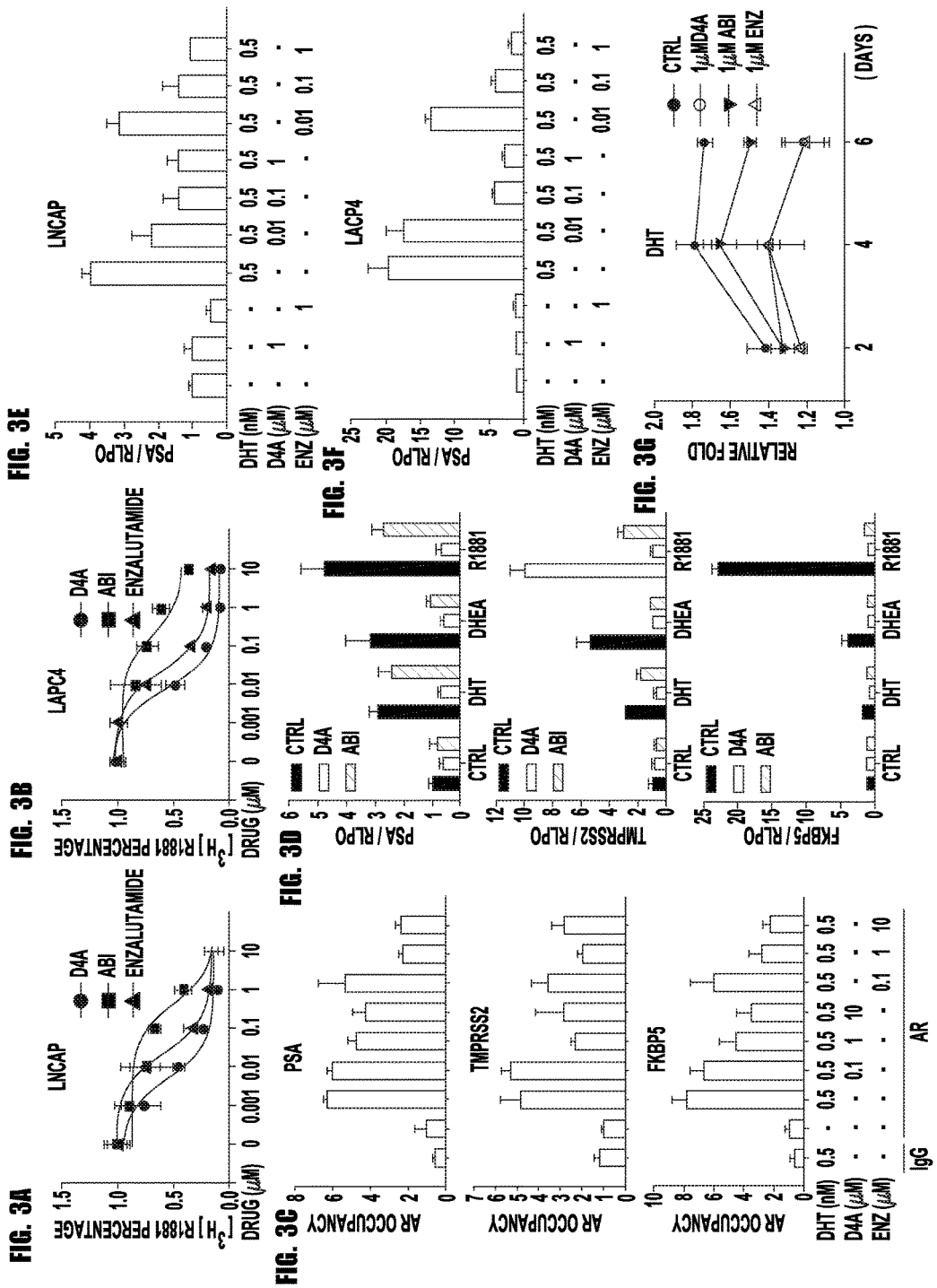

| IC50 | D4A | ABIRATERONE | ENZALUTAMIDE |
|---|---|---|---|
| CYP17A1 (nM) | 0.1 | 0.2 | N/A |
| 3βHSD1 (nM) | 19 | 140 | N/S |
| SRD5A (μM) | 1.2 | >100 | >100 |
| WT AR (nM) | 7.9 | >500 | 23 |
| MUTATED AR (nM) | 5.3 | 418 | 24 |

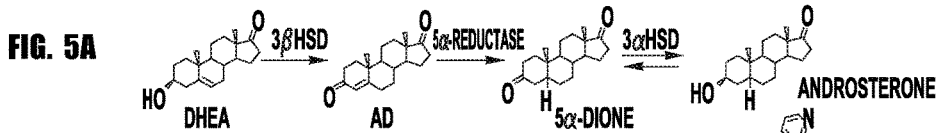
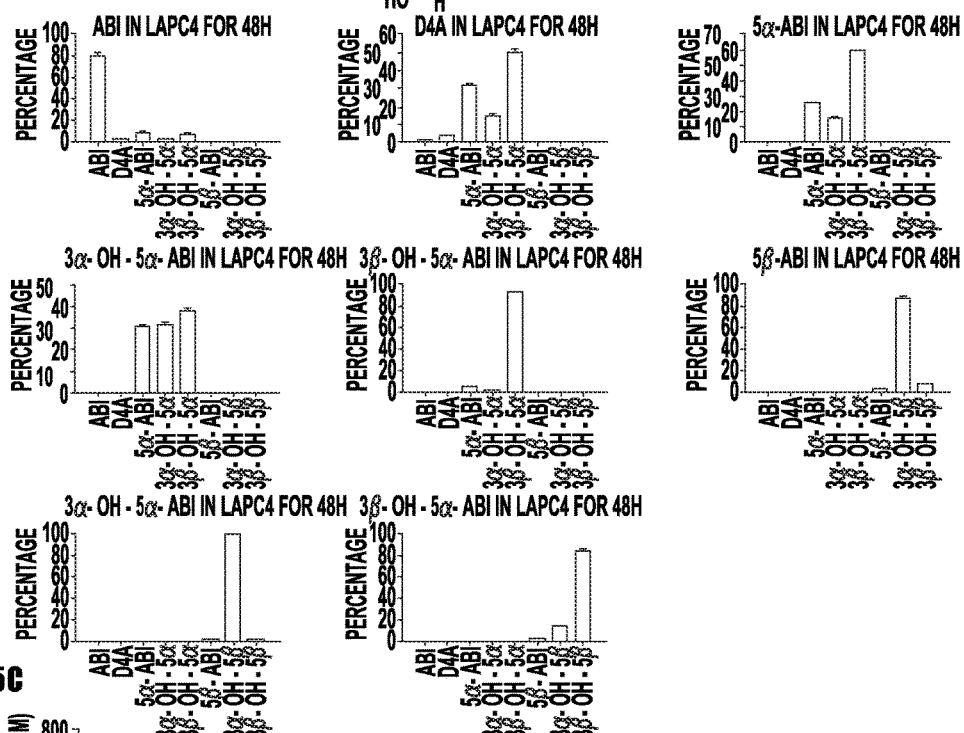
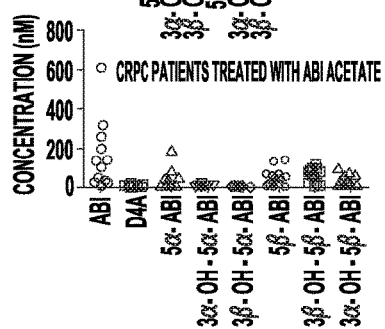

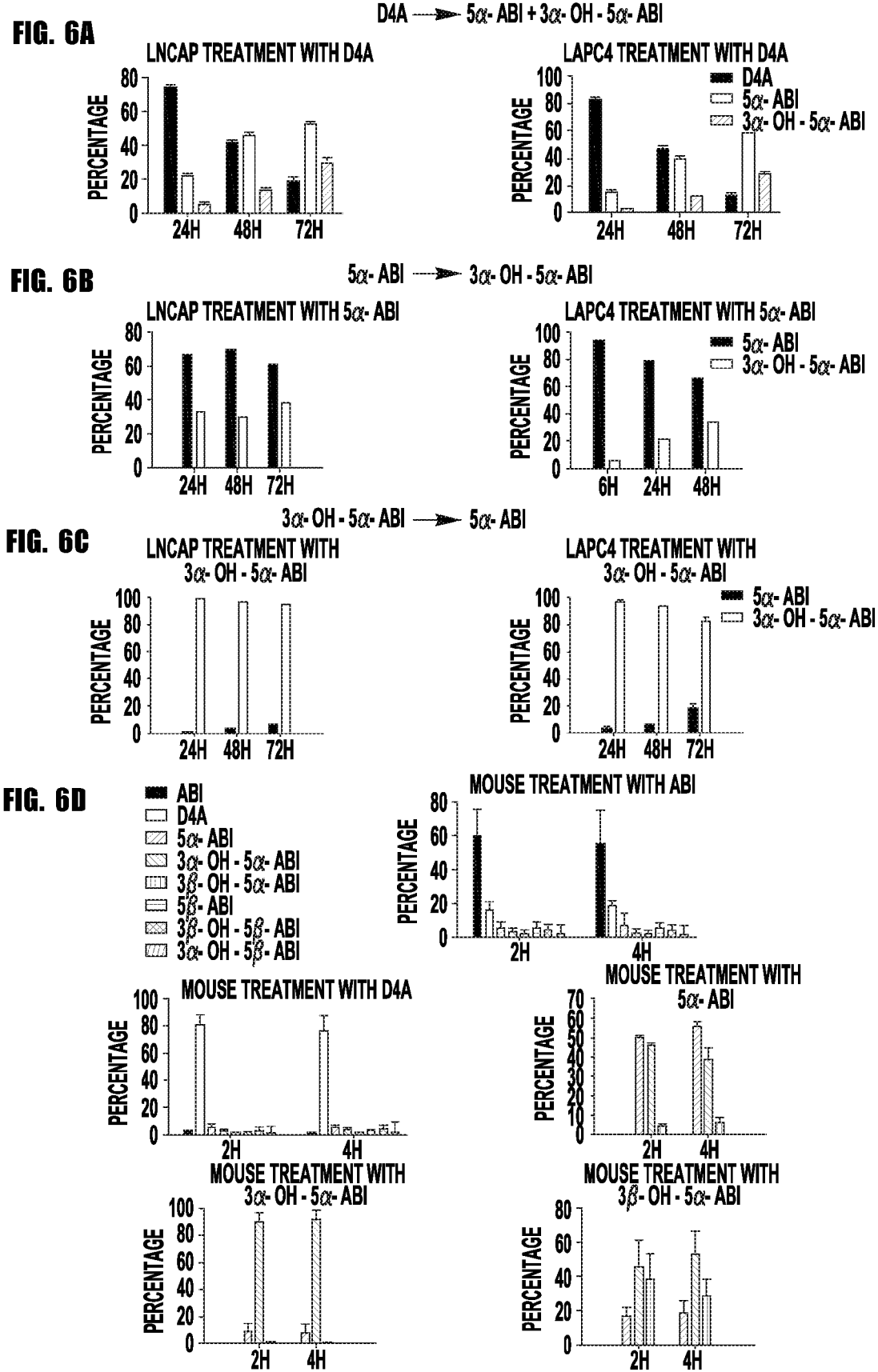

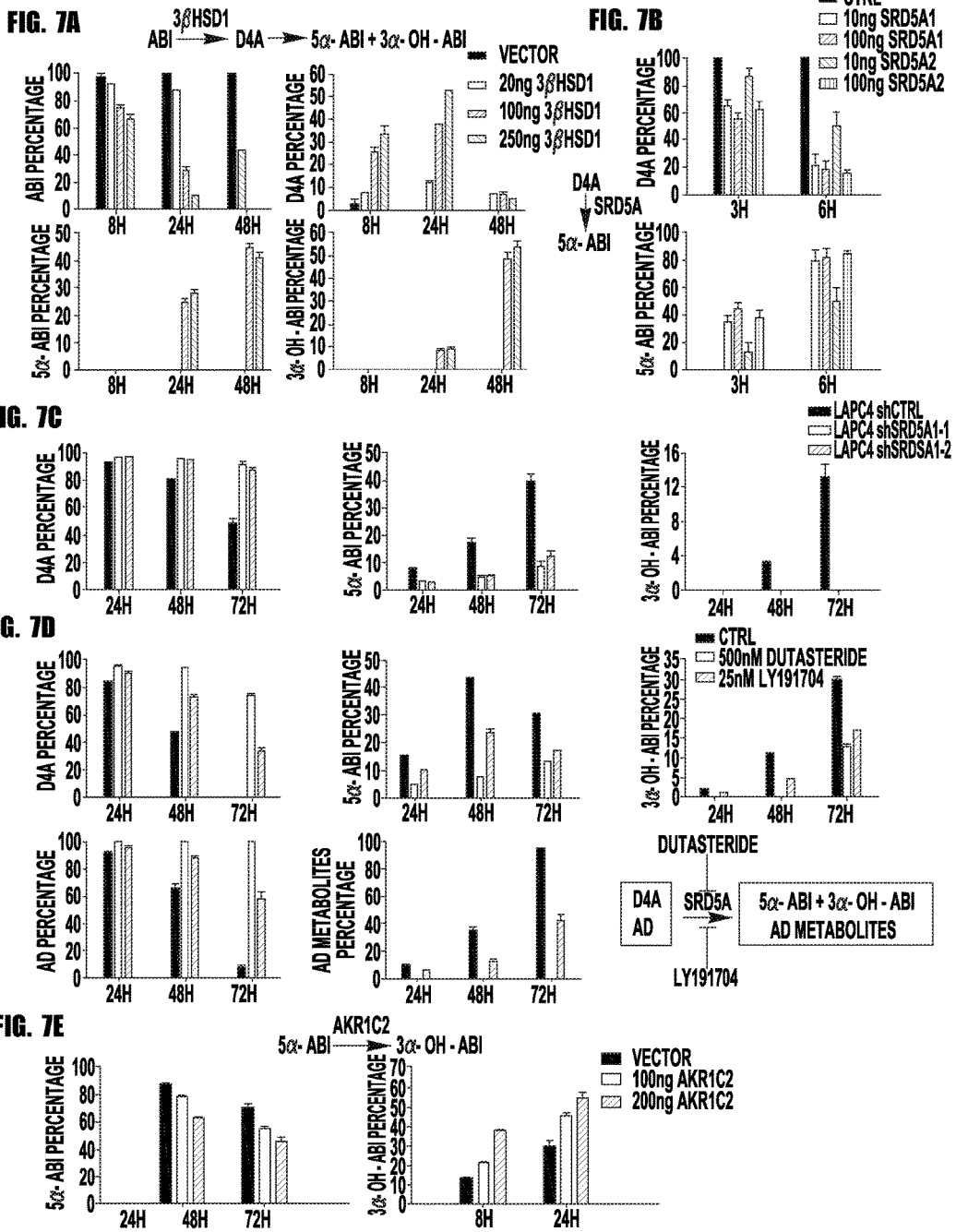

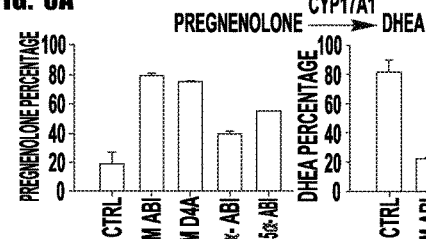
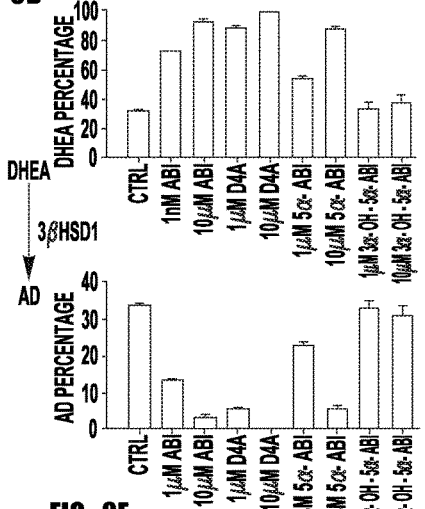
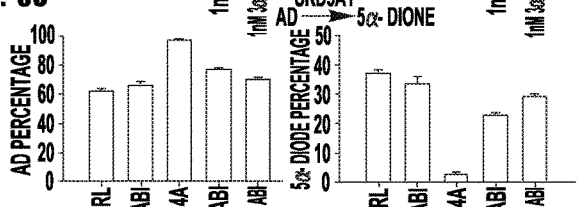
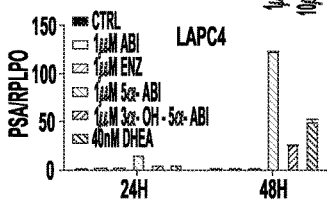
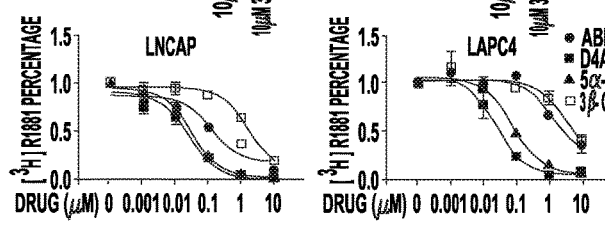
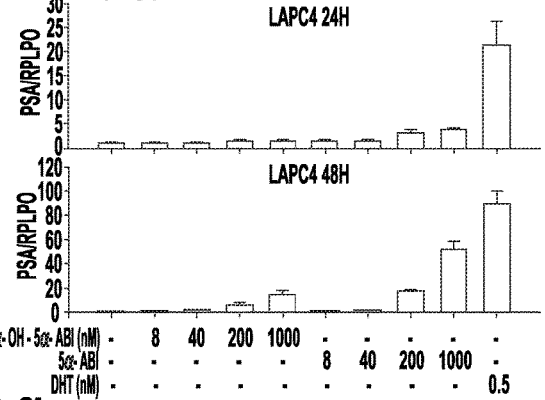
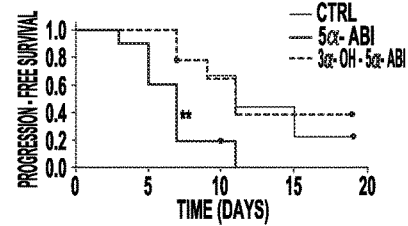
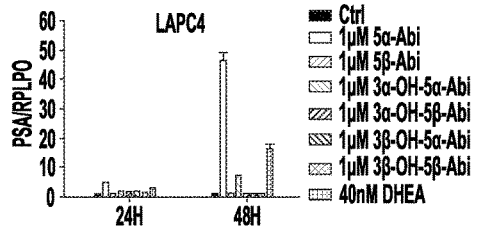

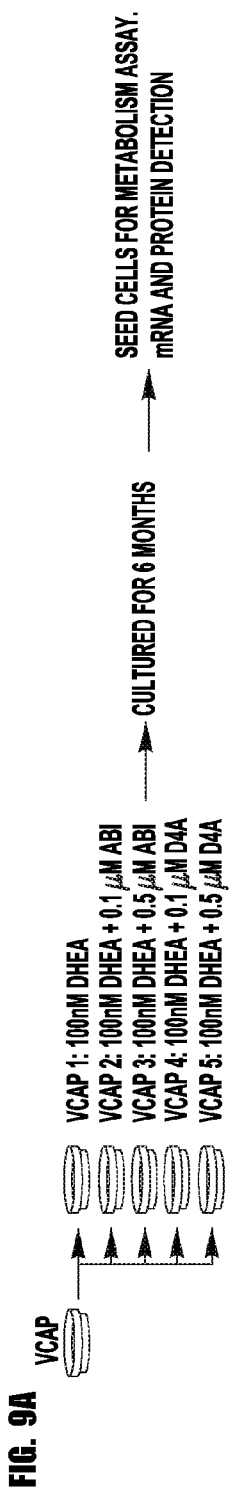

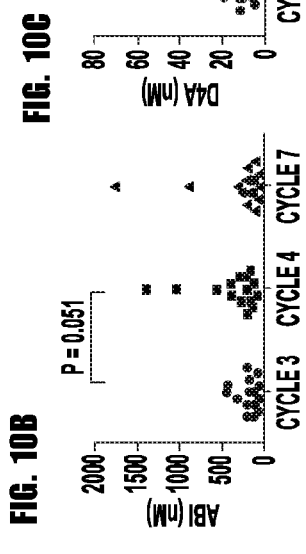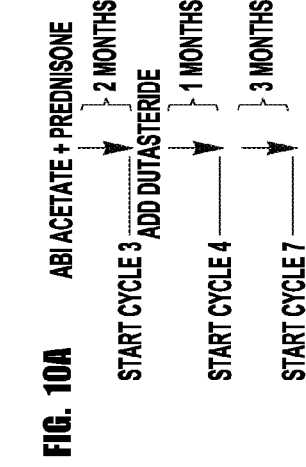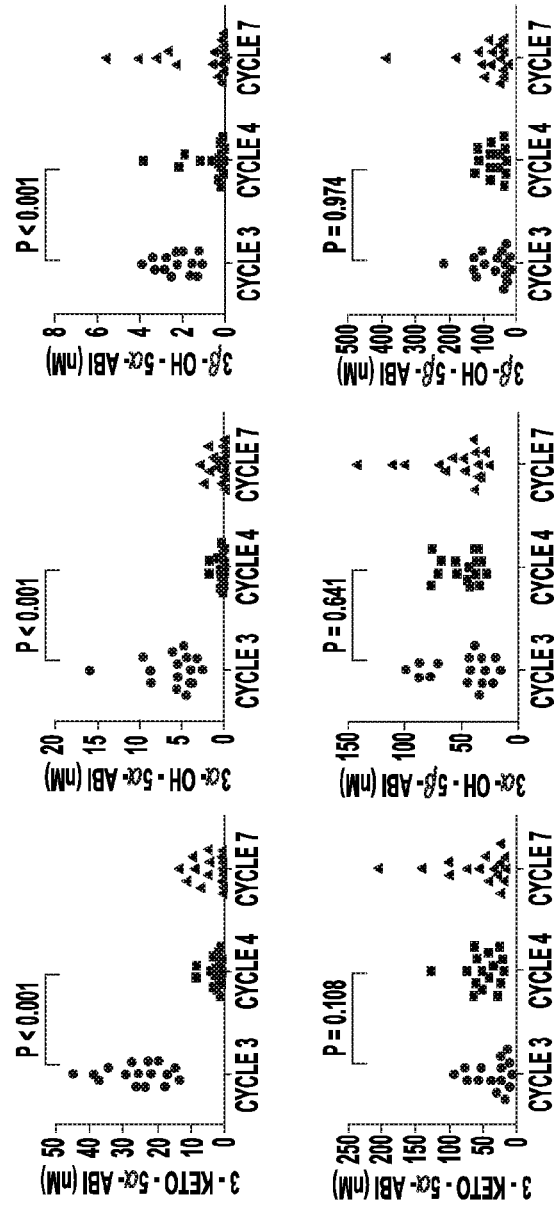

ALTERING STEROID METABOLISM FOR
TREATMENT OF STEROID-DEPENDENT
DISEASE

CROSS-REFERENCE TO RELATED APPLICATIONS

This application claims priority to U.S. Provisional Patent Application Ser. No. 62/129,215, filed Mar. 6, 2015, and U.S. Provisional Patent Application Ser. No. 62/207,594, filed Aug. 20, 2015, both of which are incorporated herein by reference.

GOVERNMENT FUNDING

The invention was made with government support under grant numbers CA168899, CA172382, and CA190289 awarded by the National Institutes of Health. The government has certain rights in the invention.

BACKGROUND

Metastatic prostate cancer generally responds initially to medical or surgical castration, followed by eventual resistance as castration-resistant prostate cancer (CRPC), which is driven by the metabolic capability of tumors to reconstitute potent androgens, mainly from dehydroepiandrosterone (DHEA)/DHEA-sulfate, and in turn stimulate the androgen receptor (AR). Chang et al., Cell 154, 1074-1084 (2013). Abiraterone (Abi; administered orally as Abi acetate), a steroidal drug, inhibits 17α-hydroxylase/17,20-lyase (CYP17A1), blocks androgen synthesis and prolongs survival, even after treatment with docetaxel chemotherapy. de Bono, et al., The New England journal of medicine 364, 1995-2005 (2011). However, resistance to abiraterone therapy can also develop. Accordingly, there remains a need for methods of treating steroid-dependent diseases such as castration-resistant prostate cancer.

SUMMARY OF THE INVENTION

Steroid-dependent diseases such as prostate cancer and breast cancer require the conversion of precursor steroids to active steroids. Prostate cancer responds initially to gonadal testosterone deprivation therapy, but eventually becomes resistant as castration-resistant prostate cancer (CRPC), which is driven by tumors converting precursor steroids (e.g., DHEA and DHEA-sulfate) to testosterone and/or dihydrotestosterone (DHT). Abiraterone, a steroidal CYP17A inhibitor, blocks this process predominantly by inhibiting the enzyme CYP17A, which is required for androgen synthesis. The inventors have shown that abiraterone is converted in subjects to D4A, a metabolite that has not previously been described, and that D4A is a more potent drug that works by blocking multiple steps along the androgen pathway. Clinical responses to abiraterone may therefore be dependent in some part on conversion to D4A. However, D4A can be metabolized further in patients and is converted by steroid 5-α-reductase to 5α-abiraterone. In contrast to the potent antitumor effects of D4A, 5α-abiraterone appears to instead stimulate the androgen receptor, which is expected to promote tumor growth. However, conversion of D4A to 5α-abiraterone can be pharmacologically blocked by 5-α-reductase inhibitors.

The inventors have discovered and developed a method of treating steroid-dependent disease in a subject in need thereof that includes administering a therapeutically effective amount a CYP17A inhibitor such as abiraterone and an effective amount of a 5-α-reductase inhibitor to the subject. In some embodiments, the steroid-dependent disease is steroid-dependent cancer such as prostate cancer or castration-resistant prostate cancer. In some embodiments, the method also includes the step of modifying treatment by using information acquired from determining the level of one or more CYP17A inhibitor metabolites in a biological sample from the subject.

BRIEF DESCRIPTION OF THE FIGURES

The present invention may be more readily understood by reference to the following figures, wherein:

FIG. 1A-FIG. 1E provides chemical structures and graphs showing the structural consequences of the conversion from Abi to D4A that occurs in both mice, and patients, and requires 3βHSD. A, Schematic of Abi conversion to D4A. * double bond and C3-position for substrates and products of 3βHSD. B, Abi is converted to D4A in vivo. Abi acetate was injected i.p. in 5 mice. Blood was collected 2 h and 4 h after injection. Serum concentrations of Abi and D4A were quantified by mass spectrometry and are represented as the percentage of the sum total of Abi+D4A. C, D4A is detectable in all patients (n=12) with CRPC treated with Abi acetate. D, Representative mass spectrometry tracing of D4A and Abi from the serum of a patient treated with Abi acetate. E, 3βHSD1 is capable of converting Abi to D4A. LAPC4 cells overexpressing 3βHSD1 were treated with 10 µM Abi (or [$^3$H]-DHEA) for 24 h. Abi, D4A (as a percentage of Abi+D4A), [$^3$H]-DHEA and [$^3$H]-DHEA metabolites (labeled metabolites), were separated by HPLC. Results are shown as mean (n=3)±s.d. with biological replicates. The experiment was repeated independently at least 3 times.

FIG. 2A-FIG. 2E provides a reaction scheme and graphs showing that D4A inhibits 3βHSD, CYP17A, and 5α-reductase enzymatic activity in the androgen pathway. A, Schematic of the steroidogenesis pathway from adrenal precursors to DHT and AR stimulation in CRPC. B, D4A inhibits 3βHSD1 activity in LNCaP. Cells were treated with [$^3$H]-DHEA with 0.1, 1 or 10 µM D4A and Abi, for 9 and 24 hours. DHEA and AD were quantified by HPLC. Arrows denote AD percentage for 0.1 µM D4A and 1 µM Abi treatment groups. C, Lineweaver-Burk plots of pregnenolone metabolism and D4A inhibition of human 3βHSD1 and 3βHSD2 activity. D4A shows mixed competitive-noncompetitive inhibition for 3βHSD1 and noncompetitive inhibition for 3βHSD2. D, CYP17A1 inhibition with D4A is comparable to Abi. 293 cells stably expressing CYP17A1 were treated with 0.1, 1 or 10 nM D4A, or Abi, together with [$^3$H]-pregnenolone for 3 and 6 hours. Pregnenolone and DHEA were separated and quantified by HPLC. E, D4A but not Abi or enzalutamide inhibits 5α-reductase activity. LAPC4 cells were treated with [3H]-AD and the indicated drug concentrations. Steroids were quantified by HPLC. Arrows denote 5α-reduced androgen percentage for 10 µM D4A and 100 µM Abi treatment groups. All experiments performed with biological replicates (n=3) and repeated independently three times. All results are shown as mean±s.d.

FIG. 3A-FIG. 3G provide graphs showing D4A binds to AR, inhibits AR chromatin occupancy, expression of AR-responsive genes and cell growth. A and B, D4A potently binds to both mutant and wild-type AR. D4A, Abi and enzalutamide (Enz) (0.001-10 µM) were used to compete with 0.1 nM [$^3$H]-R1881 for mutated AR (LNCaP) or wild type AR (LAPC4). Intracellular radioactivity was normalized to protein concentration. C, Dose-dependence of D4A versus Enz for inhibition of AR chromatin occupancy. LNCaP cells were treated with the indicated concentrations of DHT, D4A, and Enz for 3 h. AR chromatin occupancy for PSA, TMPRSS2 and FKBP5 was detected with ChIP. AR ChIP is normalized to untreated control for each gene. D, D4A inhibits PSA, FKBP5 and TMPRSS2 expression. LNCaP cells were treated with DHT (0.5 nM), DHEA (40 nM) or R1881 (0.1 nM) with or without Abi or D4A (1 μM) for 24 h. Gene expression was detected by qPCR and normalized to RPLP0. E and F, D4A inhibition of DHT induced PSA expression is comparable to Enz in LNCaP and LAPC4. g, D4A inhibits DHT (0.5 nM) induced cell growth in LNCaP. Cells were quantified at the indicated time points by assaying DNA content after 2, 4 and 6 days of treatment. Experiments in a, b and g were performed with biological replicates; c-f were performed with technical replicates. All experiments were repeated independently three times. All results are shown as mean (n=5 for panel g; n=3 for all other experiments)±s.d.

FIG. 5A-FIG. 5C provide a chemical scheme and graphs showing the genesis of 5α- and 5β-reduced Abi metabolites in patients treated with Abi acetate. (A) Abiraterone metabolism by steroidogenic enzymes. Above, in a pathway of androgen metabolism, DHEA is converted by 3βHSD to $\Delta^4$-androstenedione (AD), which is 5α-reduced to 5α-androstanedione (5α-dione), which is in turn 3-keto-reduced to androsterone. Below, structurally analogous conversion of abiraterone to D4A enables 5α- and 5β-reduction of D4A at carbon 5 (arrow), yielding 6 additional Abi metabolites. Dotted arrows indicate uncertainly of direct conversion between 3α- and 3β-isomers. (B) Interconversion of Abi metabolites in the LAPC4 prostate cancer cell line. Cells were treated with Abi or the indicated metabolite (0.1 μM) for 48 hours and each of the indicated metabolites was detected by liquid chromatography-mass spectrometry (LC-MS/MS) in triplicate. Errors bars represent the SD. (C) Abi metabolites in sera of 12 patients with prostate cancer treated with Abi acetate. Metabolites were measured by LC-MS/MS.

FIG. 6A-FIG. 6D provide graphs showing the In vitro time course and in vivo formation of 5α-reduced Abi metabolites. (A) Conversion from D4A to 5α-reduced Abi metabolites, (B) 3-keto reduction of 5α-Abi to 3α-OH-5α-Abi, and (C) 3α-OH-oxidation of 3α-OH-5α-Abi to 5α-Abi is detectable in LNCaP and LAPC4 prostate cancer cell lines. Cells were treated with 10 μM of the indicated compounds, metabolites were separated by high performance liquid chromatography (HPLC) and quantitated by UV spectroscopy. (D) In vivo Abi metabolism in mice. Treatment with Abi (n=5 mice) or D4A (n=5 mice) results in detection of all six 5-reduced metabolites. Treatment with any of the three 5α-reduced Abi metabolites (n=4 mice for each compound) results in detection of the two other 5α-reduced metabolites, demonstrating interconversion. Experiments in A-C were performed in triplicate at least 3 times and error bars represent the SD.

FIG. 7A-FIG. 7E provide graphs showing the enzymes involved in the formation of 5α-reduced Abi metabolites. (A) 3βHSD1 catalyzes the conversion of Abi to D4A and downstream accumulation of 5α-Abi and 3α-OH-5α-Abi. LAPC4 cells were transiently transfected with the indicated amount of an expression construct encoding 3βHSD1 or vector control before treatment with Abi. (B) Conversion of D4A to 5α-Abi is catalyzed by SRD5A1 or SRD5A2. The indicated amounts of SRD5A1, or SRD5A2, or empty vector plasmids were transfected into 293T cells, and cells were incubated with D4A for the designated incubation times. (C) SRD5A1 silencing blocks 5α-reduction of D4A. LAPC4 cells stably expressing shRNAs targeting SRD5A1 or non-silencing control were treated with D4A and metabolites for the indicated times. (D) Pharmacologic SRD5A inhibition blocks 5α-reduction of D4A. LAPC4 cells were treated with D4A and the SRD5A inhibitors dutasteride or LY191704. A parallel control experiment is shown with inhibition of 5α-reduction of [$^3$H]-AD. (E) Conversion of 5α-Abi to 3α-OH-5α-Abi is catalyzed by AKR1C2. 293T cells were transfected with AKR1C2 or empty vector and treated with 5α-Abi for the indicated times. For all experiments, metabolites were separated by HPLC and quantitated by UV spectroscopy (Abi metabolites) or with a beta-RAM ([$^3$H]-androgens). Error bars represent SD in all experiments. All experiments were performed at least 3 times.

FIG. 8A-FIG. 8I provide graphs showing the effects of 5α-reduced Abi metabolites on the androgen pathway and tumor progression. (A) Potent CYP17A1 inhibition activity attributable to Abi and D4A is attenuated with conversion to 5α-Abi and 3α-OH-5α-Abi. 293 cells overexpressing CYP17A1 were treated with [$^3$H]-pregnenolone and conversion to DHEA was assessed in the presence of the indicated drugs. (B) 5α-reduction of D4A causes loss of 3βHSD inhibitory activity. LNCaP cells were treated with [$^3$H]-DHEA and the indicated drugs for 48 hours, and metabolic flux to AD was assessed. (C) 5α-Abi and 3α-OH-5α-Abi lose SRD5A inhibition activity attributable to D4A. LAPC4 cells were treated with [$^3$H]-AD and the indicated drugs, and flux to 5α-dione was assessed after 24 hours of incubation. (D) 5α-Abi and D4A comparably bind to AR. LNCaP and LAPC4 express the mutated AR and wild-type AR, respectively, and were incubated with [$^3$H]-R1881 and the indicated compounds for 30 min. Intracellular radioactivity was normalized to protein concentration. (E) and (F) 5α-Abi stimulates androgen-responsive gene expression in LAPC4 and LNCaP. Delayed and more modest PSA expression is stimulated with 3α-OH-5α-Abi. (G) Dose-dependent stimulation of PSA expression by 5α-Abi in LAPC4. (H) Treatment with 5α-Abi (n=10 mice) but not 3α-OH-5α-Abi (n=9 mice) hastens VCaP CRPC xenograft growth compared with control (n=9 mice) in orchiectomized mice. Treatment with the indicated compounds began when CRPC tumors reached 100 mm³ and progression-free survival was assessed as the time at which there was >30% growth for 2 sequential measurements. The significance of the difference between treatment groups was assessed with the log rank test. ** P<0.01 for the difference between 5α-Abi and Ctrl. (I) 5β-reduced Abi metabolites do not stimulate PSA expression. Expression is normalized to RPLPO and vehicle expression in E-G and I. Error bars represent the SD in A-G and I. All experiments in A-G and I were performed at least 3 times.

FIG. 9A-FIG. 9E provide a scheme, images, and graphs showing that long-term exposure to Abi and D4A leads to an increase in SRD5A expression and enzymatic activity and an increase in conversion from D4A to 5α-reduced Abi metabolites. (A) Experimental schema. VCaP cells were cultured with DHEA (100 nM) alone, or with the indicated concentration of Abi or D4A continuously for 6 months. LNCaP cells were treated under similar conditions (LN1, LN3 and LN5=VCaP1, VCaP3 and VCaP5 treatment, respectively). Treatment with Abi or D4A induces an increase in SRD5A enzyme activity and increased conversion of D4A to 5α-Abi metabolites in (B) VCaP and (C) LNCaP. Cells were treated with [$^3$H]-AD, [$^3$H]-T, or D4A for 24 or 48 hours, and conversion to 5α-reduced metabolites was assessed by HPLC. SRD5A1 protein expression is increased with Abi and D4A treatment in (D) VCaP and (E) LNCaP. (C) and (D) were performed in triplicate with error bars representing the SD. All experiments were performed at least 3 times.

FIG. 10A-FIG. 10F provide graphs and a table showing that SRD5A inhibition significantly increases serum D4A and specifically and significantly depletes all three 5α-Abi metabolites in serum of patients treated with Abi acetate. (A) Clinical trial schema. Blood was collected for Abi metabolites after 2 months of treatment with Abi acetate+prednisone (start cycle 3), and again after 1 and 4 months (start cycles 4 and 7) of addition of treatment with dutasteride. Serum concentrations of (B) Abi, (C) D4A, (D) all three 5α-reduced Abi metabolites, (E) all three 5β-reduced Abi metabolites, in sera. (F) Table summary of mean Abi and Abi metabolite concentrations at each of the 3 time points in the clinical trial.

DETAILED DESCRIPTION OF THE INVENTION

Figure 4A:
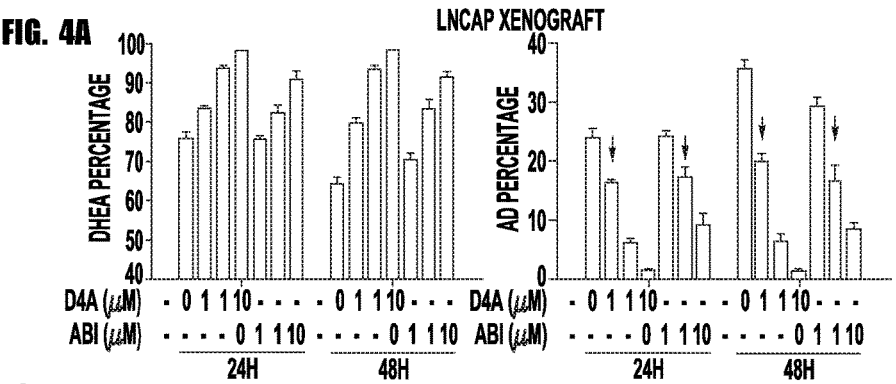
FIG. 4A-FIG. 4E provide graphs showing D4A inhibits xenograft steroidogenesis and growth. A and B, D4A inhibits steroidogenesis in LNCaP and VCaP xenografts. Xenografts were grown subcutaneously in NSG mice. Xenografts reaching ~1000 mm³ were minced and treated with [$^3$H]-DHEA, plus Abi or D4A (0.1, 1 and 10 μM). DHEA and AD were separated and quantified by HPLC. Experiments were performed with biological replicates (n=3 xenograft tissues) and results are shown as mean±s.d. Arrows denote AD percentage for 0.1 μM D4A and 1 μM Abi treatment groups. C, D4A is more potent than Abi for blocking VCaP xenograft progression. Time to xenograft progression (>20% increase in tumor volume) is shown for vehicle (Ctrl; n=9 mice), Abi acetate (AA; n=10) and D4A (n=10) treatment groups. All 3 treatment groups differ significantly from one another: Ctrl vs AA, P=0.02; Ctrl vs D4A, P<0.001; AA vs D4A, P=0.01. D, D4A (n=10) is more potent than AA (n=10) and Enz (n=11) for blocking C4-2 xenograft progression: Ctrl vs D4A, P<0.001; AA vs D4A, P=0.01; Enz vs D4A, P=0.02. E, Schematic of D4A activities and IC50 in the androgen pathway and comparisons with Abi and Enz.

The inventors have demonstrated herein that administering a therapeutically effective amount a CYP17A inhibitor and an effective amount of a 5-α-reductase inhibitor can be used to treat steroid-dependent disease such as prostate cancer in a subject.

Definitions

The terminology as set forth herein is for description of the embodiments only and should not be construed as limiting of the invention as a whole. As used in the description of the invention and the appended claims, the singular forms "a", "an", and "the" are inclusive of their plural forms, unless contraindicated by the context surrounding such.

Treat", "treating", and "treatment", etc., as used herein, refer to any action providing a benefit to a subject afflicted with a steroid-dependent disease such as prostate cancer, including improvement in the condition through lessening or suppression of at least one symptom, delay in progression of the disease, etc.

Prevention, as used herein, refers to any action providing a benefit to a subject at risk of being afflicted with a steroid-dependent disease such as prostate cancer, including avoidance of the development of the condition or disease or a decrease of one or more symptoms of the disease should a disease develop. The subject may be at risk as a result of family history.

"Pharmaceutically acceptable" as used herein means that the compound or composition is suitable for administration to a subject for the methods described herein, without unduly deleterious side effects in light of the severity of the disease and necessity of the treatment.

The term "therapeutically effective" is intended to qualify the amount of each agent which will achieve the goal of decreasing disease severity while avoiding adverse side effects such as those typically associated with alternative therapies. The therapeutically effective amount may be administered in one or more doses. An effective dose, on the other hand, is an amount sufficient to provide a certain effect, such as enzyme inhibition, but may or may not be therapeutically effective.

As used herein, the term "diagnosis" can encompass determining the nature of disease in a subject, as well as determining the severity and probable outcome of disease or episode of disease and/or prospect of recovery (prognosis). "Diagnosis" can also encompass diagnosis in the context of rational therapy, in which the diagnosis guides therapy, including initial selection of therapy, modification of therapy (e.g., adjustment of dose and/or dosage regimen), and the like.

The invention is inclusive of the active agents described herein in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

Treatment of Steroid-Dependent Disease

In one aspect, the invention provides a method of treating steroid-dependent disease in a subject in need thereof that includes administering a therapeutically effective amount a CYP17A inhibitor and an effective amount of a 5-α-reductase inhibitor to the subject.

Combined administration of a CYP17A inhibitor and a 5-α-reductase inhibitor (i.e., the active agents) can be used to provide prophylactic and/or therapeutic treatment. The active agents of the invention can, for example, be administered prophylactically to a subject in advance of the occurrence of a steroid-dependent disease. Prophylactic (i.e., preventive) administration is effective to decrease the likelihood of the subsequent occurrence of steroid-dependent disease in the subject, or decrease the severity of steroid-dependent disease that subsequently occurs. Prophylactic treatment may be provided to a subject that is at elevated risk of developing steroid-dependent disease, such as a subject with a family history of steroid-dependent disease.

Alternatively, the active agents can be administered therapeutically to a subject that is already afflicted by a steroid-dependent disease. A subject diagnosed as having a steroid-dependent disease is a subject in need of treatment. A subject in need of cancer treatment can be a subject who has been diagnosed as having a disorder characterized by unwanted, rapid cell proliferation. Such disorders include, but are not limited to cancers and precancerous conditions. In one embodiment of therapeutic administration, administration of the compounds is effective to eliminate the steroid-dependent disease; in another embodiment, administration of the active agents is effective to decrease the severity of the steroid-dependent disease or lengthen the lifespan of the subject so afflicted. The subject is preferably a mammal, such as a domesticated farm animal (e.g., cow, horse, pig) or pet (e.g., dog, cat). More preferably, the subject is a human.

Steroid-Dependent Disease

The present invention provides methods for diagnosing, treating, and guiding treatment of steroid-dependent disease. Steroid-dependent disease, as used herein, refers to diseases that depend on the presence of steroid hormones in order to persist. In particular, steroid-dependent diseases refer to diseases in which the enzyme CYP17A1 plays a role in regulating the amount of steroid upon which the disease depends. Examples of steroid-dependent diseases include asthma, hypertension, inflammatory bowel disease (e.g., Crohn's disease and ulcerative colitis), nephritic syndrome, endometriosis, adrenal dysfunction, breast cancer, and prostate cancer. As used herein, steroid-dependent disease also encompasses a disease which is normally characterized as being a steroid-dependent disease, but which has or develops steroid independence.

In some embodiments, the steroid-dependent disease is cancer. Examples of steroid-dependent cancer include bladder cancer, breast cancer, endometrial cancer, pancreatic cancer, and prostate cancer. The identification of additional types of cancer which can be steroid-dependent is ongoing. In some embodiments, the steroid upon which the cancer depends is a sex steroid. Sex steroids, also known as gonadal steroids, are steroid hormones that interact with androgen or estrogen receptors. Sex steroids include androgens such as anabolic steroids, androstenedione, dehydroepiandrosterone, dihydrotestosterone, and testosterone; estrogens such as estradiol, estriol, and estrone; and the progestogen progesterone.

As used herein, the terms "tumor" or "cancer" refer to a condition characterized by anomalous rapid proliferation of abnormal cells of a subject. The abnormal cells often are referred to as "neoplastic cells," which are transformed cells that can form a solid tumor. The term "tumor" refers to an abnormal mass or population of cells (e.g., two or more cells) that result from excessive or abnormal cell division, whether malignant or benign, and pre-cancerous and cancerous cells. Malignant tumors are distinguished from benign growths or tumors in that, in addition to uncontrolled cellular proliferation, they can invade surrounding tissues and can metastasize.

In some embodiments, the cancer is prostate cancer. Prostate cancer, as used herein, refers to a disease in which cancer develops in the prostate gland of the male reproductive system. Prostate cancer is classified as an adenocarcinoma, or glandular cancer, that begins when normal semen-secreting prostate gland cells mutate into cancer cells. In the initial stage of prostate cancer, small clumps of cancer cells remain confined to otherwise normal prostate glands, a condition known as carcinoma in situ or prostatic intraepithelial neoplasia (PIN), a prostate precancer. Over time these cancer cells begin to multiply and spread to the surrounding prostate tissue (the stroma), forming a tumor. While prostate cancer originates and may remain in the prostate, prostate tumor cells may develop the ability to travel in the bloodstream and lymphatic system and thus be found in other organs or tissues. Prostate cancer most commonly metastasizes to the bones, lymph nodes, rectum, and bladder. Treatment or prevention of prostate cancer, as used herein, also refers to the treatment of metastasized prostate cancer found in other organs or tissues.

Most steroid-dependent cancers become refractory after one to three years and resume growth despite therapy. Accordingly, in some embodiments, the prostate cancer is castration-resistant prostate cancer, which is also known as hormone-refractory prostate cancer or androgen-independent prostate cancer. Subjects who have castration-resistant prostate cancer are no longer responsive to castration treatment, which is a reduction of available androgen/testosterone/DHT by chemical or surgical means. However, these cancers still show reliance upon hormones for androgen receptor activation.

The presence of prostate cancer or other steroid-dependent diseases can be confirmed using a variety of techniques known to those skilled in the art. The preferred method for confirming the presence of prostate cancer is to obtain a biopsy. In a prostate cancer biopsy, a tissue samples from the prostate is typically obtained via the rectum using a biopsy gun which inserts and removes special hollow-core needles. The tissue samples are then examined under a microscope to determine whether cancer cells are present, and to evaluate the microscopic features or Gleason score of any cancer found. Additional procedures for determining whether a human subject has prostate cancer include, but are not limited to, digital rectal examination, cystoscopy. transrectal ultrasonography, ultrasound, and magnetic resonance imaging.

In case of cancer treatment, the method of steroid-dependent disease can further include the step of ablating the cancer. Ablating the cancer can be accomplished using a method selected from the group consisting of cryoablation, thermal ablation, radiotherapy, chemotherapy, radiofrequency ablation, electroporation, alcohol ablation, high intensity focused ultrasound, photodynamic therapy, administration of monoclonal antibodies, and administration of immunotoxins.

Active Agents

The present invention treats steroid-dependent disease using combination treatment with a CYP17A inhibitor and a 5-α-reductase inhibitor. Subjects with steroid-dependent disease can develop resistance to treatment with CYP17A inhibitors through changes in steroid metabolism. The inventors have shown that abiraterone is converted in subjects to D4A, a metabolite that has not previously been described, and that D4A is a more potent drug that works by blocking multiple steps along the androgen pathway. Clinical responses to abiraterone may therefore be dependent in some part on conversion to D4A. However, D4A can be metabolized further in patients and is converted by steroid 5-α-reductase to 5-α-abiraterone. In contrast to the potent antitumor effects of D4A, 5-α-abiraterone appears to instead stimulate the androgen receptor, which is expected to promote tumor growth. However, conversion of D4A to 5-α-abiraterone can be pharmacologically blocked by 5-α-reductase inhibitors.

Because the 5-α-reductase inhibitor derives a significant portion of its effectiveness from its ability to overcome resistance to the CYP17A inhibitor used for treatment of steroid-dependent disease, the CYP17A inhibitor and a 5-α-reductase inhibitor should be administered close enough together in time for the 5-α-reductase inhibitor to increase the effectiveness of the CYP17A inhibitor. This can be referred to herein as being administered proximately in time. What constitutes proximately in time can vary with the metabolism of the individual, and the dose of the CYP17A inhibitor and 5-α-reductase inhibitor being administered. In some embodiments, proximate in time can be within 1 hour, within 6 hours, within 12 hours, or within 24 hours of administration of the other agent. In some embodiments, the CYP17A inhibitor and 5-α-reductase inhibitor are administered simultaneously. However, in other embodiments, the 5-α-reductase inhibitor can be administered proximately in time either before or after CYP17A inhibitor administration, or proximately in time before CYP17A inhibitor administration, or proximately in time after CYP17A inhibitor administration.

The CYP17A and 5-α-reductase inhibitors may be administered as a pair, or in conjunction with other drugs or nutrients, as in an adjunct therapy. The phrase "adjunct therapy" or "combination therapy" in defining use of a compound described herein and one or more other pharmaceutical agents, is intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations for each agent.

A number of CYP17A inhibitors are known and suitable for use in the method. Cytochrome P450 17A (CYP17A), also known as steroid 17-alpha-monooxygenase, or 17α-hydroxylase/17,20 lyase/17,20 desmolase, is an enzyme that in humans is encoded by the CYP17A1 gene. It has both 17alpha-hydroxylase and 17,20-lyase activities, and is a key enzyme in the steroidogenic pathway that produces progestins, mineralocorticoids, glucocorticoids, androgens, and estrogens. Examples of CYP17A inhibitors include abiraterone, the abiraterone metabolite D4A, galeterone, orteronel, VT-464, and CFG920. See Gomez et al., Steroids, 95, 80-87 (2015). In some embodiments, the CYP17A inhibitor is a steroidal compound selected from the group consisting of abiraterone, the abiraterone metabolite D4A, and galeterone, while in further embodiments the CYP17A inhibitor is selected from the group consisting of abiraterone and the abiraterone metabolite D4A.

A wide variety of 5-α-reductase inhibitors are known and suitable for use in the method. These agents inhibit the enzyme 5α-reductase, which is involved in the metabolic transformations of a variety of endogenous steroids. 5α-reductases, also known as 3-oxo-5α-steroid 4-dehydrogenases, are enzymes involved in steroid metabolism. There are three isoenzymes of 5-alpha reductase (1, 2, and 3), which vary in different tissues with age. 5α-reductase inhibition is most known for preventing conversion of testosterone, the major androgen sex hormone, to the more potent dihydrotestosterone (DHT), in androgen-associated disorders. In some embodiments, the 5-α-reductase inhibitor is selected from the group consisting of dutasteride, finasteride, lapisteride, turosteride, bexlosteride, izonsteride, and epristeride.

Candidate agents may be tested in animal models. The animal model should be one appropriate for the steroid-dependent disease being treated, such as prostate cancer. For example, the animal model can be one for the study of cancer. The study of various cancers in animal models (for instance, mice) is a commonly accepted practice for the study of human cancers. For instance, the nude mouse model, where human tumor cells are injected into the animal, is commonly accepted as a general model useful for the study of a wide variety of cancers (see, for instance, Polin et al., Investig. New Drugs, 15:99-108 (1997)). Results are typically compared between control animals treated with candidate agents and the control littermates that did not receive treatment. Transgenic animal models are also available and are commonly accepted as models for human disease (see, for instance, Greenberg et al., Proc. Natl. Acad. Sci. USA, 92:3439-3443 (1995)). Candidate agents can be used in these animal models to determine if a candidate agent decreases one or more of the symptoms associated with the cancer, including, for instance, cancer metastasis, cancer cell motility, cancer cell invasiveness, or combinations thereof.

Modifying Treatment by Determining the Level of One or More CYP17A Inhibitor Metabolites Another embodiment of the method includes the step modifying treatment by determining the level of one or more CYP17A inhibitor metabolites in a biological sample from the subject. The levels of CYP17A inhibitor metabolites can be used to evaluate whether treatment with the 5-α-reductase inhibitor should be modified. In other words, the CYP17A inhibitor metabolites are used as biomarkers to monitor the effectiveness of therapy. Modifying treatment includes, for example, changing the 5-α-reductase inhibitor being administered, changing the administration schedule, or changing the dose of 5-α-reductase or CYP17A inhibitor being administered. The metabolites are typically steroid metabolites. For example, when abiraterone is administered, CYP17A inhibitor metabolites include steroid metabolites selected from the group consisting of D4A, 3β-OH-5β-abi, 3-keto-5α-abi, 3-keto-5β-abi, 3α-OH-5α-abi, 3α-OH-5β-abi, and 3β-OH-5α-abi.

In some embodiments, the method includes determining levels of one or more CYP17A inhibitor metabolites in a biological sample taken from the subject prior to therapy and then determining levels of CYP17A inhibitor metabolites in a corresponding biological sample taken from the subject during or following therapy. Alternately, the method can include determining levels of one or more CYP17A inhibitor metabolites in a biological sample taken from the subject before or after therapy and comparing them with predetermined values. Typically, and increased level of CYP17A inhibitor metabolite formation is a sign that treatment should be modified, though it some situations specific increased metabolites can be a positive indicator showing that inhibition of steroid synthesis to treat the steroid-dependent disease is being maintained.

Biological samples include, but are not necessarily limited to bodily fluids such as urine and blood-related samples (e.g., whole blood, serum, plasma, and other blood-derived samples), urine, cerebral spinal fluid, bronchoalveolar lavage, and the like. Another example of a biological sample is a tissue sample. The levels of CYP17A inhibitor metabolites in a biological sample taken from the subject can be assessed either quantitatively or qualitatively, usually quantitatively. The levels of CYP17A inhibitor metabolites can be determined either in vivo or in vitro.

A biological sample may be fresh or stored (e.g. blood or blood fraction stored in a blood bank). Samples can be stored for varying amounts of time, such as being stored for an hour, a day, a week, a month, or more than a month. The biological sample may be a bodily fluid expressly obtained for the assays of this invention or a bodily fluid obtained for another purpose which can be subsampled for the assays of this invention.

The levels of CYP17A inhibitor metabolites in a subject can be measured using an analytic device, which is a machine including a detector capable of identifying steroids and fragments thereof. The analytic device may be a spectrometric device, such as a mass spectrometer, an ultraviolet spectrometer, or a nuclear magnetic resonance spectrometer. A spectrometer is a device that uses a spectroscopic technique to assess the concentration or amount of a given species in a medium such as a biological sample (e.g., a bodily fluid). The analytic device used to measure the levels of CYP17A inhibitor metabolites can be either a portable or a stationary device. In addition to including equipment used for detecting CYP17A inhibitor metabolites, the analytic device can also include additional equipment to provide purification (i.e., physical separation) of analytes prior to analysis. For example, if the analyte detector is a mass spectrometer, it may also include a high performance liquid chromatograph (HPLC) or gas chromatograph (GC) to purify the CYP17A inhibitor metabolites before their detection by mass spectrometry, or it may be preferable to purify the protein using gel electrophoresis.

As indicated herein, mass spectrometry-based methods can be used to assess levels of CYP17A inhibitor metabolites in a biological sample. Mass spectrometers include an ionizing source (e.g., electrospray ionization), an analyzer to separate the ions formed in the ionization source according to their mass-to-charge (m/z) ratios, and a detector for the charged ions. In tandem mass spectrometry, two or more analyzers are included. Such methods are standard in the art and include, for example, HPLC with on-line electrospray ionization (ESI) and tandem mass spectrometry.

In some embodiments, the levels of CYP17A inhibitor metabolites in the biological sample obtained from a test subject is compared to a predetermined value. In one embodiment, the predetermined value is based upon the levels of CYP17A inhibitor metabolites in comparable samples obtained from a pool of subjects being administered CYP17A inhibitor. These control subjects can also be receiving a 5-α-reductase inhibitor, or alternately may not be receiving a 5-α-reductase inhibitor.

The comparison can be conducted by any suitable method known to those skilled in the art. For example, the comparison can be carried out mathematically or qualitatively by an individual operating the analytic device or by another individual who has access to the data provided by the analytic device. Alternately, the steps of determining and comparing the levels of CYP17A inhibitor metabolites can be carried out electronically (e.g., by an electronic data processor).

Administration and Formulation

The present invention also provides pharmaceutical compositions that include a CYP17A inhibitor and a 5-α-reductase inhibitor as active ingredients, and a pharmaceutically acceptable liquid or solid carrier or carriers, in combination with the active ingredients. Any of the compounds described above as being suitable for the treatment of steroid-dependent disease can be included in pharmaceutical compositions of the invention.

The compounds can be administered as pharmaceutically acceptable salts. Pharmaceutically acceptable salt refers to the relatively non-toxic, inorganic and organic acid addition salts of the compounds. These salts can be prepared in situ during the final isolation and purification of the compound, or by separately reacting a purified compound according to formula I with a suitable counterion, depending on the nature of the compound, and isolating the salt thus formed. Representative counterions include the chloride, bromide, nitrate, ammonium, sulfate, tosylate, phosphate, tartrate, ethylenediamine, and maleate salts, and the like. See for example Haynes et al., J. Pharm. Sci., 94, p. 2111-2120 (2005). For example, a preferred salt form of abiraterone is abiraterone acetate.

The pharmaceutical compositions include one or more active ingredients together with one or more of a variety of physiological acceptable carriers for delivery to a subject, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the active agent into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The CYP17A inhibitor and 5-α-reductase inhibitor can be administered as a single dose or in multiple doses. Useful dosages of the active agents can be determined by comparing their in vitro activity and their in vivo activity in animal models. Methods for extrapolation of effective dosages in mice, and other animals, to humans are known in the art; for example, see U.S. Pat. No. 4,938,949.

The agents of the present invention are preferably formulated in pharmaceutical compositions and then, in accordance with the methods of the invention, administered to a subject, such as a human patient, in a variety of forms adapted to the chosen route of administration. The formulations include, but are not limited to, those suitable for oral, inhaled, rectal, vaginal, topical, nasal, ophthalmic, or parenteral (including subcutaneous, intramuscular, intraperitoneal, and intravenous) administration.

In some embodiments, one or more of the CYP17A inhibitor and/or the 5-α-reductase inhibitor are administered orally. Formulations of the present invention suitable for oral administration may be presented as discrete units such as tablets, troches, capsules, lozenges, wafers, or cachets, each containing a predetermined amount of the active agent as a powder or granules, as liposomes containing the active compound, or as a solution or suspension in an aqueous liquor or non-aqueous liquid such as a syrup, an elixir, an emulsion, or a draught. Such compositions and preparations typically contain at least about 0.1 wt-% of the active agent. The amount of the compound according to formula I (i.e., active agent) is such that the dosage level will be effective to produce the desired result in the subject.

Inhaled formulations include those designed for administration from an inhaler device. Compositions for inhalation or insufflation include solutions and suspensions in pharmaceutically acceptable, aqueous or organic solvents, or mixtures thereof, aerosols, and powders. Preferably, the compositions are administered by the oral or nasal respiratory route for local or systemic effect. Compositions in preferably pharmaceutically acceptable solvents may be nebulized by use of inert gases. Solution, suspension, or powder compositions may be administered, preferably orally or nasally, from devices that deliver the formulation in an appropriate manner. Nasal spray formulations include purified aqueous solutions of the active agent with preservative agents and isotonic agents. Such formulations are preferably adjusted to a pH and isotonic state compatible with the nasal mucous membranes.

Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Preparation of the Compounds

Compounds of the invention may be synthesized by synthetic routes that include processes similar to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

Those skilled in the art will appreciate that various synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

The present invention is illustrated by the following examples. It is to be understood that the particular examples, materials, amounts, and procedures are to be interpreted broadly in accordance with the scope and spirit of the invention as set forth herein.

EXAMPLES

Example 1: Conversion of Abiraterone to D4A Drives Antitumor Activity in Prostate Cancer Prostate cancer resistance to castration occurs because tumors acquire the metabolic capability of converting precursor steroids to 5α-dihydrotestosterone (DHT), promoting signaling by the androgen receptor (AR) and the development of castration-resistant prostate cancer (CRPC). Chang et al., Cell, 154:1074-1084 (2013). Essential for resistance, DHT synthesis from adrenal precursor steroids or possibly from de novo synthesis from cholesterol commonly require enzymatic reactions by 3β-hydroxysteroid dehydrogenase (3βHSD), steroid-5α-reductase (SRD5A) and 17β-hydroxysteroid dehydrogenase (17βHSD) isoenzymes. Knudsen K E, Penning T M., Trends Endocrinol Metab. 21:315-324 (2010). Abiraterone, a steroidal 17α-hydroxylase/17,20-lyase (CYP17A1) inhibitor, blocks this synthetic process and prolongs survival. Ryan et al., N Engl J Med. 368(2): 138-48, (2012). We hypothesized that abiraterone is converted by an enzyme to the more active Δ4-abiraterone (D4A) that blocks multiple steroidogenic enzymes and antagonizes the androgen receptor (AR), providing an additional explanation for abiraterone's clinical activity. Here we show that abiraterone is converted to D4A in mice and patients with prostate cancer. D4A inhibits CYP17A1, 3βHSD and SRD5A, which are required for DHT synthesis. Furthermore, competitive AR antagonism by D4A is comparable to the potent antagonist, enzalutamide. D4A also has more potent antitumor activity against xenograft tumors than abiraterone. Our findings suggest an additional explanation—conversion to a more active agent—for abiraterone's survival extension. We propose that direct treatment with D4A would be more clinically effective than abiraterone treatment.

The central role and critical requirement for androgen metabolism and AR in CRPC are demonstrated by the clinical benefit and overall survival benefit conferred by abiraterone (Abi), which blocks CYP17A1, an enzyme required for androgen synthesis, and enzalutamide, which potently and competitively blocks the AR. Beer et al., N Engl J Med., 371(5):424-33 (2014). Abi (administered in its acetate form for bioavailability) is a steroidal compound and is therefore potentially subject to conversion by steroid-metabolizing enzymes. We hypothesized the $\Delta^5$, 3β-hydroxyl-structure of Abi, which is also present in the natural steroid substrates dehydroepiandrosterone (DHEA) and $\Delta^5$-androstenediol (A5diol), makes it susceptible to one enzyme conversion by 3βHSD isoenzymes to its $\Delta^4$, 3-keto congener ($\Delta^4$-abiraterone or D4A), which would make the steroid A and B rings identical to testosterone (T), enabling inhibitory interactions with AR and additional steroidogenic enzymes, including SRD5A, which are required for DHT synthesis (FIG. 1a). Such a conversion in peripheral tissues would allow D4A to engage with multiple targets to potentiate its effects on the androgen pathway, providing an alternative explanation for the clinical efficacy of Abi therapy and thus the possibility that direct treatment might be more efficacious.

We found that D4A is detectable in the sera of mice administered Abi acetate (FIG. 1b), as well as in sera from patients with CRPC who were undergoing treatment with Abi acetate (FIGS. 1c, 1d). In the LAPC4 prostate cancer cell line, which usually has low 3βHSD activity, conversion of Abi to D4A is detectable only if 3βHSD is overexpressed (FIG. 1e). Other tissues such as the mouse adrenal (but not mouse prostate) that have robust endogenous 3βHSD enzymatic activity also convert Abi to D4A. These results suggest that D4A is a major metabolite of Abi, requires 3βHSD for conversion, and may confer effects on the tumor that are indirectly due to Abi.

D4A may impinge on multiple steps in the androgen pathway, including CYP17A1, 3βHSD, SRD5A and direct interaction with AR (FIG. 2a). Although augmented Abi drug exposure may block 3βHSD, normal dosing probably does not. Li et al., Clin Cancer Res. 18:3571-3579 (2012). On the other hand, D4A is approximately 10-fold more potent than Abi at blocking the conversion of [$^3$H]-DHEA by 3βHSD to $\Delta^4$-androstenedione (AD) in LNCaP and VCaP cells, as assessed by thin layer chromatography (TLC) and high performance liquid chromatography (HPLC; FIG. 2b). D4A inhibits both human isoenzymes, 3βHSD1 and 3βHSD2, with mixed inhibition kinetics (FIG. 2c). CYP17A1 inhibition is the major direct mechanism of action for Abi. Ferraldeschi et al., Clin Cancer Res. 19:3353-3359 (2013). Structural studies of modified steroidal azoles suggest that the A-ring conformation of D4A does not significantly perturb binding to CYP17A1. Garrido et al., J Steroid Biochem Mol Biol., 143:1-10 (2014). D4A and Abi similarly block conversion of [$^3$H]-pregnenolone by CYP17A1 to DHEA (% conversion to DHEA after 3 h incubation for vehicle, 1 nM D4A and 1 nM Abi is 70.1%, 4.2% and 2.6%, respectively) by HPLC in intact 293 cells expressing CYP17A1 (FIG. 2d). The $\Delta^4$, 3-keto-structure of D4A is identical to physiologic SRD5A substrates, such as T and AD (FIG. 1a). Chang et al., Proc Natl Acad Sci USA., 108:13728-13733 (2011). To determine the effect of D4A on endogenously expressed SRD5A, LAPC4 cells, which exhibit robust SRD5A enzymatic activity were treated with D4A, Abi or enzalutamide, and cultured in the presence of [$^3$H]-AD (the preferred natural substrate of SRD5A1). D4A (10 μM) nearly completely blocks conversion from AD to 5α-androstanedione and other 5α-reduced androgens, whereas Abi and enzalutamide have no detectable effect even at a concentration of 100 μM (FIG. 2e).

Abi has been reported to have modest affinity for AR, particularly in the presence of mutations in the ligand-binding domain (LBD). Richards et al., Cancer Res. 72:2176-2182 (2012). Conversion of Abi by 3βHSD to D4A would provide a 3-keto structure, which is shared with both T and DHT, steroids with the highest affinity for AR (FIG. 1a). To determine how conversion from Abi to the 3-keto structure of D4A affects drug affinity for AR, we performed a competition assay. The affinity of D4A for mutant (expressed in LNCaP, $IC_{50}$=5.3 nM) and wild-type (expressed in LAPC4, $IC_{50}$=7.9 nM) AR is greater than that of Abi ($IC_{50}$=418 and >500 nM, respectively), comparable to or slightly greater than that of enzalutamide ($IC_{50}$=24 and 23 nM, respectively, FIGS. 3a-b), and clearly greater than bicalutamide, which was the most potent competitive non-steroidal AR antagonist prior to the introduction of enzalutamide. The affinity of D4A for the AR LBD translates to inhibition of DHT-induced AR chromatin occupancy on the PSA, TMPRSS2 and FKBP5 regulatory elements on chromatin, which is superior to Abi and somewhat lower than enzalutamide (FIG. 3c). The incongruity between AR affinity and effects on chromatin occupancy for D4A and enzalutamide is consistent with combined AR antagonism and chromatin binding in an inactive complex as previously reported for some AR antagonists. Hodgson et al., J Biol Chem. 280:6511-6519 (2005).

We next examined the cumulative results of the effects of D4A on androgen-responsive gene expression. Compared to Abi, D4A clearly better suppresses PSA, TMPRSS2 and FKBP5 expression induced by DHT, DHEA and R1881 in LNCAP, LAPC4 and C4-2 cell lines (FIG. 3d). D4A inhibits AR target gene expression in a dose-dependent manner. Comparisons of D4A to enzalutamide on DHT-induced endogenous PSA expression demonstrate that D4A is equivalent to enzalutamide against mutant and wild-type AR (FIGS. 3e-f). Downstream of androgen-responsive gene expression, effects of D4A and enzalutamide on DHT-stimulated cell growth are equivalent (FIG. 3g), both of which are more potent than Abi.

Figure 4B:
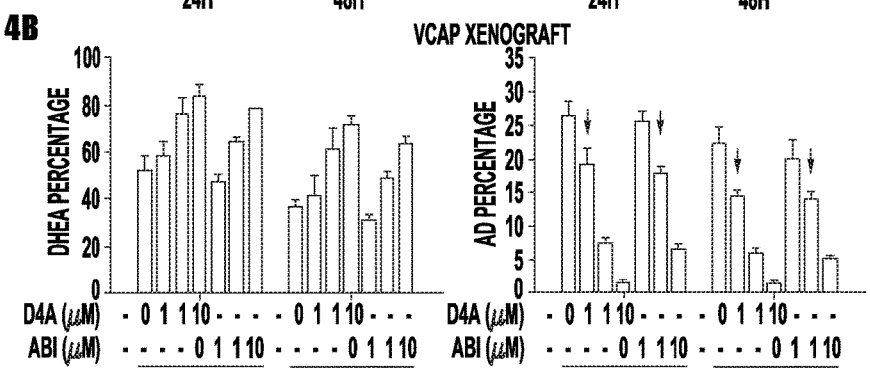
Figure 4C:
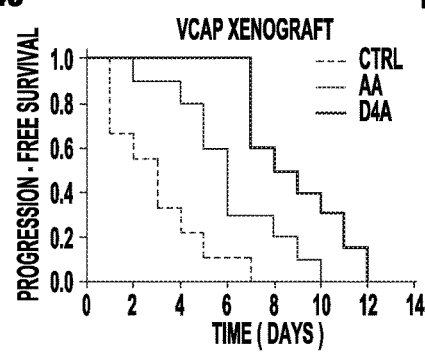
Figure 4D:
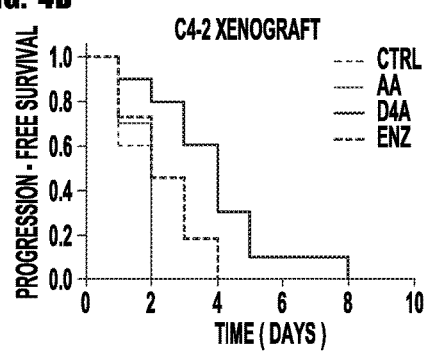
Figure 4E:
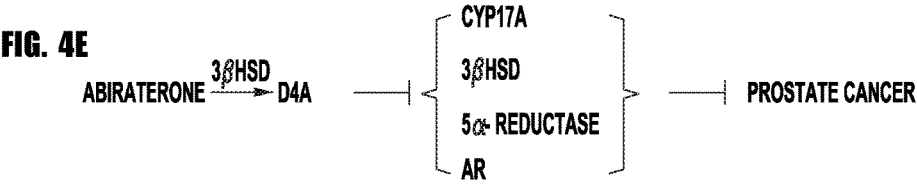

To determine whether the observed effects of D4A on inhibition of steroid synthesis demonstrated in tissue culture also occur in tumors, effects in two prostate cancer xenograft models with robust 3βHSD enzymatic activity were assessed. Subcutaneous mouse xenograft tumors of VCaP and LNCaP cells, which both harbor a mutant gene encoding a missense in 3βHSD1 that effectively increases enzyme activity, were grown in male NSG mice. Fresh tumors were harvested, minced and incubated with [$^3$H]-DHEA plus Abi or D4A (0.1-10 μM). Similar to effects shown in FIG. 2, D4A is 10-fold more potent than Abi in blocking conversion from DHEA by 3βHSD to AD in LNCaP (FIG. 4a) and VCaP xenografts (FIG. 4b). For example, 0.1 μM D4A is equivalent to 1 μM Abi for blocking AD accumulation at 48 hr in both LNCaP and VCaP xenografts. To test whether the combined effects of D4A on inhibition of steroid synthesis and direct blockade of AR lead to augmented anti-tumor activity compared with Abi, VCaP xenografts were grown subcutaneously in orchiectomized mice with DHEA pellet implantation (to mimic human adrenal physiology; FIG. 4c). Time from initiation of treatment with D4A, Abi acetate or vehicle, to tumor progression (>20% increase in tumor volume) was assessed by generating Kaplan-Meier survival curves and comparing treatment groups with the log-rank test. Progression was significantly delayed in the D4A group compared to the Abi acetate group (P=0.011). We also compared xenograft growth using the same method with the C4-2 cell line model. D4A treatment increased progression-free survival compared to Abi acetate and enzalutamide (FIG. 4d). In serum collected from D4A treated mice at the end of the xenograft study there was no detectable increase in deoxycorticosterone, which is the mineralocorticoid that is most highly elevated in patients treated with Abi acetate, causing hypertension and hyperkalemia. Attard et al., J Clin Oncol. 26:4563-4571 (2008). FIG. 4e depicts the multiple points in the androgen pathway at which conversion of Abi by 3βHSD to D4A in patients impinges on AR signaling and prostate cancer progression, and the relative potencies of D4A, Abi and enzalutamide.

The next-generation hormonal therapies, Abi and enzalutamide, each have a single predominant target (CYP17A1 and AR, respectively). These drugs have clinically validated that androgen synthesis and AR stimulation are both essential components required to spur the development and progression of CRPC. After oral administration, Abi acetate is hydrolyzed and thereby converted to Abi, which is thought to be the major active agent by way of blocking CYP17A1. The major recognized metabolites of Abi result from hepatic CYP3A4 and SULT2A1 processing, forming the N-oxide of Abi and Abi sulfate, respectively. Neither of these modifications affects the $\Delta^5$, 3β-hydroxyl-structure of the steroid backbone. In contrast, conversion to D4A modifies the steroidal structure to one that more robustly engages with AR, SRD5A and 3βHSD, thereby blocking androgen signaling at all these steps, while retaining CYP17A1 inhibition. The clinical significance of conversion of Abi to D4A and effects on individual components of the androgen pathway in patients must be viewed in light of pharmacokinetic studies which show a $C_{max}$ of approximately 1 µM and also wide interpatient variability. Furthermore, our findings suggest that D4A also has much more potent anti-tumor activity against CRPC when directly compared to Abi.

The potential clinical utility of treating CRPC patients directly with D4A is dependent on the underlying mechanisms of resistance to Abi, which have not been fully elucidated and the clinical settings in which the benefit from Abi is exhausted. The evidence suggests that sustained AR signaling characterizes at least a subset of Abi resistance cases. For example, increased AR copy number in CRPC is associated with absence of clinical response to Abi (Carreira et al., Sci Transl Med. 6:254ra125 (2014)) and increased AR protein expression appears to occur upon the development of acquired clinical resistance to Abi. Although Abi is a potent CYP17A1 inhibitor, studies of urinary steroid metabolites in patients demonstrate that androgen synthesis inhibition is incomplete, raising the possibility of sustained steroidogenesis as a mechanism of resistance. Attard et al., J Clin Endocrinol Metab. 97:507-516 (2012). Clinically, the combination of CYP17A1 inhibition and a potent AR antagonist appears to confer more potent androgen signaling inhibition in patients with CRPC. Efstathiou et al., ASCO Meeting Abstracts, 32:5000 (2014).

Circulating concentrations of D4A in patients treated with Abi acetate appear to be quite variable. In contrast to hepatic Abi metabolites, it is probable that conversion of Abi to D4A in peripheral tissues leads to D4A concentrations that are higher in peripheral tissues (such as CRPC) than are present in serum. The effects of D4A on androgen signaling in CRPC, in particular distal steps in DHT synthesis and activity as an AR antagonist, may therefore be underestimated based on serum concentrations alone. Nonetheless, D4A levels in peripheral tissues and the precise contribution of D4A to the clinical activity of Abi have yet to be determined.

Finally, our results raise the possibility that there may be a previously unappreciated class effect of steroidal versus nonsteroidal CYP17A1 inhibitors. In contrast to Abi acetate, TAK-700, a nonsteroidal CYP17A1 inhibitor, failed to prolong survival in metastatic CRPC. Fizazi et al., J Clin Oncol. 33(7):723-31 (2015). It is possible that the absence of active downstream steroidal metabolites may have contributed to these findings. This issue should be considered as other steroidal and nonsteroidal CYP17A1 inhibitors undergo further clinical investigation.

In conclusion, we have identified a novel Abi metabolite that is present in patients with CRPC treated with Abi acetate and has more potent anti-tumor activity than the parent drug. Conversion to D4A may be responsible for some of the clinical activity observed with the use of Abi. We suggest that treatment with D4A is likely to result in a greater clinical benefit than Abi.

Methods

Cell Lines

LNCaP and VCaP cells were purchased from the American Type Culture Collection (Manassas, Va.) and maintained in RPMI-1640 with 10% FBS. LAPC4 cells were kindly provided by Dr. Charles Sawyers (Memorial Sloan Kettering Cancer Center, New York, N.Y.) and grown in Iscove's Modified Dulbecco's Medium with 10% FBS. C4-2 cells were kindly provided by Dr. Leland Chung (Cedars-Sinai Medical Center, Los Angeles, Calif.) and maintained in RPMI-1640 with 10% FBS. All experiments done with LNCaP and VCaP were done in plates coated with poly-DL-ornithine (Sigma-Aldrich, St. Louis, Mo.). A 293 cell line stably expressing human CYP17A1 was generated by transfection with plasmid pcDNA3-CYP17 (a generous gift of Dr. Walter Miller, University of California, San Francisco) and selection with G418. Cell lines was authenticated by DDC Medical (Fairfield, Ohio) and determined to be negative mycoplasma free with primers.

Chemicals

Abi acetate was purchased from Medkoo Biosciences (Chapel Hill, N.C.). Abi and D4A were synthesized as described previously. Li et al., Clin Cancer Res. 18:3571-3579 (2012). Enzalutamide was obtained from Medivation (San Francisco, Calif.).

Steroid Metabolism

Cell Line Metabolism: Cells were seeded and incubated in 12-well plates with 0.2 million cells/well for ~24 h and then incubated with a mixture of radioactive ([$^3$H]-labeled) and non-radioactive androgens (final concentration, 100 nM; ~1,000,000 cpm/well; PerkinElmer, Waltham, Mass.) at 37° C. Aliquots of medium were collected at the indicated times. Collected medium was treated with 1,000 units of β-glucuronidase (Helix pomatia; Sigma-Aldrich) at 65° C. for 2 h, extracted with 860 µL ethyl acetate:isooctane (1:1), and concentrated under nitrogen gas. Xenograft Metabolism: $10^7$ LNCaP or VCaP cells were injected subcutaneously with Matrigel into surgically orchiectomized NSG mice that were implanted with 5 mg 90-day sustained-release DHEA pellets (Innovative Research of American, Sarasota, Fla.). Xenografts were harvested when they reached 1000 mm$^3$, minced, and cultured in DMEM with 10% FBS at 37° C. with mixture of radioactive ([$^3$H]-labeled) and non-radioactive androgens, or Abi, when they reached 1000 mm$^3$. Each xenograft was analyzed in triplicate in at least three independent experiments. Aliquots of medium were collected at the indicated times. Collected medium was treated with 1,000 units of β-glucuronidase at 65° C. for 2 h, extracted with 860 µL ethyl acetate:isooctane (1:1), and concentrated under nitrogen gas.

High-performance liquid chromatography (HPLC) analysis was performed on a Waters 717 Plus HPLC or an Agilent 1260 HPLC. Dried samples were reconstituted in 50% methanol and injected into the HPLC. Steroids and drug metabolites were separated on Kinetex 100×2.1 mm, 2.6 µm particle size $C_{18}$ reverse-phase column (Phenomenex, Torrance, Calif.) using a methanol/water gradient at 30° C. The column effluent was analyzed using a dual-wavelength UV-visible detector set at 254 nm or β-RAM model 3 in-line radioactivity detector (IN/US Systems, Inc.) using Liquiscint scintillation cocktail (National Diagnostics, Atlanta, Ga.). Alternatively, dried samples were applied to plastic-backed silica gel plates and separated by thin-layer chromatography (TLC) using a mobile phase of 3:1 chloroform: ethyl acetate, followed by exposure of the plates to a phosphorimager screen and quantitated with a Storm model 860 phosphorimager (Applied Biosystems, Foster City, Calif.). All HPLC and TLC studies were conducted in triplicate and repeated at least 3 times in independent experiments. Results are shown as mean±SD.

Gene Expression

Cells were starved with phenol red-free and serum free-medium for at least 48 h and treated with the indicated drugs and/or androgens. RNA was extracted with a GenElute Mammalian Total RNA miniprep kit (Sigma-Aldrich). cDNA was synthesized from 1 µg RNA in a reverse transcription reaction using the iScript cDNA Synthesis Kit (Bio-Rad, Hercules, Calif.). Quantitative PCR (qPCR) analysis was conducted in triplicate with primers for PSA, TMPRSS2, FKBP5, and RPLPO described previously (Chang et al., Cell, 154:1074-1084 (2013), with an ABI 7500 Real-Time PCR machine (Applied Biosystems) using iTaq Fast SYBR Green Supermix with ROX (Bio-Rad) in 96-well plates at a final reaction volume of 20 μL. Accurate quantitation of each mRNA was achieved by normalizing the sample values to RPLPO and to vehicle-treated cells.

ChIP Assay

LNCaP cells were serum-starved for at least 48 h and treated with indicated drugs and DHT for 3 h. A ChIP assay was performed with an anti-AR antibody (Santa Cruz, sc-816) as described previously. Li et al., Proc Natl Acad Sci USA. 108:3116-3123 (2011). All of the precipitated DNA samples were quantified by qPCR and normalized to input DNA. All ChIP experiments were performed at least three times. Primers used for ChIP experiments are from experiments previously described. Evaul et al., Endocrinology, 151:3514-3520 (2010).

Mouse Xenograft Studies

Male NSG mice, 6 to 8 weeks of age were obtained from the Cleveland Clinic Biological Resources Unit facility. All mouse studies were conducted under a protocol approved by the Cleveland Clinic Institutional Animal Care and Use Committee. Sample size was determined based on our prior studies of steroidogenesis inhibition in xenograft models of CRPC. Chang et al., Proc Natl Acad Sci USA., 108:13728-13733 (2011). Criteria for progression were determined based on similar criteria that are utilized for clinical progression. Mice were surgically orchiectomized and implanted with a 5 mg 90-day sustained-release DHEA pellet (Innovative Research of America) to mimic CRPC in the context of human adrenal physiology. Two days later, $10^7$ VCaP or C4-2 cells were injected subcutaneously with matrigel. Once tumors reached 300 mm$^3$ (length×width×height×0.52), mice were arbitrarily (but not strictly randomized) assigned to vehicle (n=9 or 10 mice for VCaP and C4-2 respectively), Abi acetate (n=10 mice for both cell lines), D4A (n=10 mice for both cell lines) or enzalutamide (n=11 for C4-2) treatment groups. Abi acetate and D4A (0.5 mmol/kg/d in 0.1 mL 5% benzyl alcohol and 95% safflower oil solution) were administered via 5 mL/kg intraperitoneal injection every day for up to 15 days. Control groups were administered 0.1 mL 5% benzyl alcohol and 95% safflower oil solution via intraperitoneal injection every day. Mice in enzalutamide group were fed with enzalutamide in chow every day (10 mg/Kg/day). Tran et al., Science. 324:787-790 (2009). Treatment was not blinded to the investigator. Tumor volume was measured daily, and time to increase in tumor volume by 20% was determined. Mice were sacrificed at treatment day 15 or when the tumor size was 2-fold greater than baseline. The significance of the difference between treatment groups was assessed by Kaplan-Meier survival analysis using a log-rank test in SigmaStat 3.5.

Enzyme Assays

To test D4A as an inhibitor of 3βHSD, enzyme assays were performed as described previously. Li et al., Clin Cancer Res. 18:3571-3579 (2012). Briefly, incubations were prepared with recombinant human 3βHSD1 or 3βHSD2 (in yeast microsomes, 45 or 2.5 μg protein per incubation, respectively), [$^3$H]-pregnenolone (100,000 cpm, 1-20 μmol/L), and D4A (5-20 μmol/L) or ethanol vehicle in 0.5 mL of potassium phosphate buffer (pH 7.4). After a pre-incubation at 37° C. for 1 to 3 min, NAD (1 mmol/L) was added, and the incubation was conducted at 37° C. for 20 min. The reaction was stopped by addition of 1 mL ethyl acetate: isooctane (1:1), and the steroids were then extracted into the organic phase and dried. The steroids in the dried extracts were resolved by HPLC and quantitated by in-line scintillation counting AR Competition Assay Cells were cultured in serum-free medium for 48 h and then treated with [$^3$H]-R1881 and the indicated concentrations of D4A, Abi, enzalutamide, R1881 or bicalutamide for 30 min. Cells were washed with 1×PBS 4 times and 0.9% NaCl solution twice before lysis with RIPA buffer. Intracellular radioactivity was measured with a Beckman Coulter LS60001C liquid scintillation counter and normalized to the protein concentration as detected with a Wallac Victor2 1420 Multilabel counter (Perkin Elmer).

Cell Proliferation Assay

LNCaP cells (0.1 million/mL) were seeded in 96-well plates and cultured in phenol red free RPMI-1640 mediums plus 10% charcoal stripped FBS with androgens and/or drugs. Medium was changed every other day. After 2, 4 or 6 days, cells were collected and lysed after treatment. Growth was then determined based on DNA content as detected by Hoechst stain and a Wallac Victor2 1420 Multilabel counter (Perkin Elmer). Two-tailed student's t-test was used to determine significance.

Mass Spectrometry

Patient serum collection and drug extraction. Twelve patients with CRPC undergoing treatment with Abi acetate were consented under an Institutional Review Board—approved protocol (Case 7813). Blood was collected using Vacutainer Plus serum blood collection tubes (#BD367814, Becton Dickenson, Franklin Lakes, N.J.). Blood was collected between 2 and 14 hours after the 1000 mg daily dose of Abi acetate was administered. Blood was allowed to clot and tubes were centrifuged at 2500 RPM for 10 minutes. Serum aliquots were frozen at −80° C. until processing. Drug metabolites and internal standard ($d_4$-cortisol, CDN isotopes Pointe-Claire, Quebec Canada) were extracted from 200 μL of patient serum with methyl tert-butyl ether (Sigma Aldrich, St. Louis, Mo.), evaporated under a stream of nitrogen gas and reconstituted in methanol prior to mass spectrometry analysis.

Mouse serum collection, derivatization and extraction. At the completion of the mouse xenograft study, mouse serum was collected for steroid analysis. 20 μl of serum and internal standard ($d_8$-deoxycorticosterone) was derivatized with hydroxylamine (Sigma Aldrich, St. Louis, Mo.). Steroids were extracted with methyl tert-butyl ether (Sigma Aldrich, St. Louis, Mo.), evaporated under a stream of nitrogen gas and reconstituted in methanol:water (50:50) prior to mass spectrometry analysis.

Stable Isotope Dilution Liquid Chromatography Mass Spectrometry Analysis

Mouse serum analysis. Samples were analyzed on a Thermo TSQ Quantiva-Prelude SPLC system (Thermo Scientific, Waltham, Mass.) with Aria MX 2.1 and Tracefinder 3.2.368.22 software for instrument controls and quantitation. Analyte separation was achieved with a Accucore 50×3 mm, 2.6 μm C18 column (Thermo Scientific, Waltham, Mass.) using a mobile phase of LCMS grade methanol and water (Thermo Scientific, Waltham, Mass.), a gradient of 25-100% methanol, and a flow rate of 0.6 ml/min. Steroids were ionized by electrospray ionization and in positive ion mode. Multiple reaction monitoring was used to follow mass transitions for the oximes of deoxycorticosterone (m/z: 361.2/124.1) and $d_8$-deoxycorticosterone (m/z: 369.4/128.1) (Steraloids Newport, R.I.). Concentrations were determined using stable isotope dilution analysis.

Patient serum analysis. Blood was obtained from prostate cancer patients with consent under a protocol approved by the Cleveland Clinic Institutional Review Board. Samples were analyzed on a ultra high-performance liquid chromatography station (Shimadzu, Kyoto, Japan) with a DGU-20A3R degasser, 2 LC-30AD pumps, a SIL-30AC autosampler, a CTO-10A column oven and a CBM-20A system controller in tandem with a QTRAP 5500 mass spectrometer (AB Sciex, Framingham, Mass.). The mobile phase consisted of LC-MS grade (Fisher) methanol: acetonitrile: water (44:36:20). Separation of drug metabolites was achieved using a Zorbax Eclipse plus 150×2.1 mm, 3.5 μm C18 column (Agilent, Santa Clara, Calif.) at a flow rate of 0.2 ml/min. Drug metabolites were ionized using electrospray ionization in positive ion mode. Multiple reaction monitoring was used to follow mass transitions for D4A (m/z: 348.2/156.3), abiraterone (m/z: 350.3/156.1), and $d_4$-cortisol (m/z: 367.1/121.1). Standard curves were generated using human serum spiked with known concentrations of each metabolite to enable determination of unknown concentrations in patient samples.

Example 2: Redirecting Abiraterone Metabolism to Biochemically Fine Tune Prostate Cancer Therapy Abiraterone is metabolized in patients to D4A, which has even greater anti-tumor activity and structural similarities to endogenous steroidal 5α-reductase substrates, such as testosterone. Here, we show that D4A is converted to at least three 5α-reduced and three 5β-reduced metabolites. The initial 5α-reduced metabolite, 3-keto-5α-abi, is more abundant than D4A in patients with prostate cancer taking abiraterone, and is an androgen receptor (AR) agonist, which promotes prostate cancer progression. In a clinical trial of abiraterone alone, followed by abiraterone plus dutasteride (a 5α-reductase inhibitor), 3-keto-5α-abi and downstream metabolites are depleted, while D4A concentrations rise, effectively blocking production of a tumor promoting metabolite and permitting D4A accumulation. Furthermore, dutasteride does not deplete three 5β-reduced metabolites, which were also clinically detectable, demonstrating the specific biochemical effects of pharmacologic 5α-reductase inhibition on abiraterone metabolism. Our findings suggest a previously unappreciated and biochemically specific method of clinically fine tuning abiraterone metabolism to optimize therapy.

Results

The $\Delta^4$, 3-keto structure of D4A makes it potentially susceptible to 5α-reduction to 3-keto-5α-Abi (5α-Abi) or 5β-reduction to 3-keto-5β-abi (5β-Abi), which are both irreversible reactions (FIG. 5A). 3-keto-reduction of both of these metabolites may reversibly convert them to their 3α-OH and 3β-OH congeners, making a total of 6 novel metabolites downstream of D4A (FIG. 5A). Conversion from Abi and D4A to all 3 5α-reduced metabolites, interconversion among the three 5α-reduced metabolites, and interconversion among the 3 5β-reduced metabolites are detectable in the LAPC4 prostate cancer cell line by mass spectrometry (FIG. 5B). Findings are similar with treatment of the VCaP cell line model of prostate cancer. Furthermore, all six metabolites are clinically detectable in the sera of 12 patients with CRPC undergoing treatment with Abi acetate (FIG. 5C).

Steroid 5α-reduction preserves the steroid planar structure and plays an essential role in the regulation of biologically active androgens (i.e., conversion of testosterone to DHT and $\Delta^4$-androstenedione [AD] to 5α-androstanedione [5α-dione]). Chang et al., Proc Natl Acad Sci USA., 108, 13728-13733 (2011). On the other hand, steroid 5β-reduction disrupts the planar conformation by introducing a 90° bend, which generally inactivates steroid hormones and facilitates clearance. We therefore focused subsequent studies on the pathway and metabolites of D4A 5α-reduction. In the LNCaP and LAPC4 human prostate cancer cell lines, and VCaP xenografts, direct incubations with D4A result in conversion to 5α-Abi and 3α-OH-5α-Abi (FIG. 6A) and treatment with 5α-Abi yields conversion to 3α-OH-5α-Abi (FIG. 6B). Particularly in LAPC4, the reversibility of this reaction is demonstrable by 5α-Abi detection upon 3α-OH-5α-Abi treatment (FIG. 6C); however, it appears that reduction to 3α-OH-5α-Abi appears to be the preferred directionality. Similarly, in vivo, 5α-Abi is preferentially converted to 3α-OH-5α-Abi, although the reverse reaction is also detectable (FIG. 6D). 3β-OH-5α-Abi is also oxidized to 5α-Abi and converted to 3α-OH-5α-Abi. Reflecting the irreversible nature of steroid 5α-reduction, no Abi, D4A, or 5β-reduced metabolites are detectable after treatment with any of the 5α-reduced Abi metabolites. Together, these data support a model in which once D4A is 5α-reduced to 5α-Abi, 3-keto reduction to both 3-(α and β)-OH isomers and the reverse reactions occur, both in prostate cancer cells and in vivo.

5α-Abi and 3α-OH-5α-Abi synthesis is facilitated by upstream conversion of Abi to D4A by 3βHSD (FIG. 7A). In cells without endogenous steroid-5α-reductase (SRD5A) expression, conversion of D4A to 5α-Abi is enabled by expression of either SRD5A1 or SRD5A2 (FIG. 7B). In LAPC4 cells, which predominantly express SRD5A1, genetically silencing SRD5A1 (FIG. 7C) or pharmacologic blockade with the SRD5A1 inhibitor LY191704 (Hirsch et al., Proc Natl Acad Sci USA., 90, 5277-5281(1993)), or clinically achievable concentrations of the dual isoenzyme inhibitor dutasteride (Clark et al., J Clin Endocrinol Metab., 89, 2179-2184 (2004)), blocks conversion of D4A to 5α-Abi and 3α-OH-5α-Abi (FIG. 7D). The aldo-keto reductase isoenzyme AKR1C2 is thought to be the predominant 3-keto reductase that converts the 3-keto steroid, DHT, to 5α-androstane-3α,17β-diol. Rizner et al., Endocrinology 144, 2922-2932 (2003). We found that AKR1C2 expression also enables the reduction of 5α-Abi to 3α-OH-5α-Abi (FIG. 7E).

Next, we sought to determine the activities of 5α-Abi metabolites on the androgen pathway. 5α-reduction of D4A to 5α-Abi and 3α-OH-5α-Abi is accompanied by attenuation or loss of CYP17A1 (FIG. 8A), 3βHSD (FIG. 8B) and SRD5A inhibition activity (FIG. 8C), as assessed by conversion from [$^3$H]-pregnenolone to DHEA, [$^3$H]-DHEA to AD, and [$^3$H]-AD to 5α-dione, respectively. The effects, or lack thereof, for D4A and 5α-Abi metabolites on 3βHSD, are consistent with observations of others that endogenous $\Delta^4$, 3-keto-steroids inhibit 3βHSD and 5α-reduction leads to loss of inhibitory activity. Byrne et al., J Clin Endocrinol Metab. 62, 413-418 (1986).

The affinity of 5α-Abi is comparable to that of D4A for the T877A mutant AR in LNCaP and wild-type AR in LAPC4, whereas the affinities of 3α-OH-5α-Abi and Abi are lower (FIG. 8D). To assess the consequences of 5α-Abi binding to AR, expression of androgen-responsive genes was assessed. Treatment with 5α-Abi results in expression of androgen-responsive genes in LAPC4 and LNCaP (FIGS. 8E, F and G). A lower level of induction occurs with 3α-OH-5α-Abi treatment. The delayed and modest effect of 3α-OH-5α-Abi on induction of PSA is consistent with low binding affinity for AR and modest conversion of 3α-OH- 5α-Abi to 5α-Abi that appears to occur to a greater extent in LAPC4 compared with LNCaP (FIG. 6C). To test the effect of AR stimulation by 5α-Abi on tumor growth, CRPC xenografts were treated with 5α-Abi and 3α-OH-5α-Abi. 5α-Abi significantly shortened progression-free survival (P<0.01), whereas 3α-OH-5α-Abi had no detectable effect when compared to control xenografts (FIG. 8H). We also tested all three 5β-reduced Abi metabolites for effects on androgen-responsive gene expression and confirmed that perturbation of the steroid planar structure is accompanied by the absence of metabolite activity (FIG. 8I).

We hypothesized that under conditions of Abi treatment, prostate cancer cells might develop the capacity to hasten the conversion of D4A→5α-Abi by SRD5A up-regulation. VCaP and LNCaP cells were cultured for 6 months with D4A or Abi, along with DHEA, to mimic the human adrenal androgen milieu (FIG. 9A). Cells propagated in long-term culture with D4A and Abi exhibited increased SRD5A enzyme activity, as assessed by conversion of [$^3$H]-AD→5α-reduced androgens, [$^3$H]-T→DHT, and D4A→5α-reduced Abi metabolites (FIGS. 9B-C). Increased SRD5A enzyme activity was accompanied by a predominant increase in SRD5A1 mRNA and protein expression (FIGS. 9D-E). Together, these results suggest that there is probably a selective growth advantage for depleting the anti-tumor activity associated with D4A and/or increasing the AR agonist activity of increased 5α-Abi concentrations.

Next, we hypothesized that the increased ratio of 5α-Abi:D4A of approximately 2.5:1 is specifically and clinically reversible by dual SRD5A isoenzyme inhibition with dutasteride in patients on treatment with Abi acetate. A phase II clinical trial (NCT01393730) of Abi acetate (1000 mg daily) plus prednisone (5 mg daily) for 2 months (2 cycles), followed by the addition of dutasteride at the start of cycle 3 (3.5 mg once daily; FIG. 10A) is ongoing in men with metastatic CRPC. Sixteen patients who had blood collected on Abi acetate alone (start of cycle 3) and after the addition of dutasteride (start of cycles 4 and 7) were included in the analysis. Strikingly, there was an 89% decline in the mean concentration of 5α-Abi after the addition of dutasteride (cycle 3: 25.8 nM vs. cycle 4: 2.9 nM; FIG. 10D). Further corroborating the effects of dutasteride on blocking 5α-reduction of D4A in patients, the other two 5α-reduced metabolites downstream of SRD5A exhibited similar declines (92% decline in 3α-OH-5α-Abi and 73% decline in 3β-OH-5α-Abi). Pharmacologic SRD5A inhibition nearly doubled the mean serum concentration of D4A (cycle 3: 9.9 nM vs. cycle 4: 18.2 nM; FIG. 10C). Unexpectedly, the addition of dutasteride also nearly doubled the mean concentration of Abi (cycle 3: 191.2 nM vs. cycle 4: 372.4 nM; FIG. 10B), although this difference did not reach statistical significance (P=0.051). Concentrations of Abi, D4A and 5α-Abi metabolites at cycle 7, the second time point after addition of dutasteride, were similar to cycle 4, although the changes from Abi alone at baseline were slightly lessened (FIG. 10F). Finally, and in sharp contrast to the substantial decline in 5α-Abi metabolites after the addition of dutasteride, there was no decrease in any of the three 5β-reduced Abi metabolites, supporting a very specific biochemical effect of SRD5A inhibition on 5α-Abi metabolism (FIG. 10E). Together, these findings demonstrate that the elevated ratio of 5α-Abi:D4A is pharmacologically, specifically and clinically reversible with dutasteride.

DISCUSSION

Although Abi is a clinically potent treatment for CRPC, resistance eventually occurs. CYP17A1 inhibition by Abi is clinically incomplete, as has been demonstrated by residual urinary androgen metabolites (Attard et al., J Clin Endocrinol Metab., 97, 507-516 (2012)) and high residual serum concentrations of DHEA-sulfate, the major androgen produced from the human adrenal, which together persist in patients on Abi treatment. Comprehensive genomic studies have shown that molecular aberrations that sustain AR signaling partake in the development of CRPC (Robinson, et al. Cell 161, 1215-1228 (2015)) and other clinical studies of circulating tumor DNA and circulating tumor cell signaling in patients treated with Abi suggest that maintained AR axis signaling drives Abi resistance. Carreira et al., Sci Transl Med., 6, 254ra125 (2104). Together, these studies suggest that reversal of sustained AR signaling should have a therapeutic benefit in at least a subset of patients with Abi resistant disease.

A component of sustained AR signaling occurs by way of a continuous supply of endogenous androgens (testosterone and/or DHT) provided by maintained steroidogenesis. Preclinical models indeed suggest that Abi resistance can be driven by an up-regulation of steroidogenic enzymes. Mostaghel et al., Clin Cancer Res., 17(18):5913-25 (2011). Our findings demonstrate that along with providing potent endogenous androgens, steroidogenic enzymes may serve a dual purpose by also regulating Abi metabolism, specifically by hastening the elimination of the anti-tumor activity associated with D4A by converting it with increased SRD5A enzyme activity to 5α-Abi, which instead has tumor-promoting AR agonist activity. Consistent with our findings, SRD5A has been noted by others as one of the most up-regulated steroidogenic enzyme transcripts in another model of Abi resistance.

The coordinate effects of steroidogenic enzymes on endogenous steroids vs. Abi should be considered in view of our findings on extensive steroidogenic metabolism of Abi. For example, increased SRD5A enzyme activity should have concordant favorable effects on tumor growth by increasing DHT synthesis and converting D4A to 5α-Abi. On the other hand, increasing 3βHSD activity would be expected to have discordant effects, as it is required for synthesis of T and DHT (beneficial to tumor) but increases conversion of Abi to D4A (detrimental to tumor). In this context, the likelihood is that the net effect of increased intratumoral 3βHSD activity is probably beneficial, because the endogenous substrates (i.e., DHEA, $\Delta^5$-androstenediol and pregnenolone) are probably preferred over D4A. A third enzymatic reaction that is relevant both to endogenous 5α-reduced androgens and 5α-Abi is 3α-OH-oxidation to 3-ketosteroids. Oxidation or 'back conversion' of (3α-OH) 5α-androstanediol, which does not stimulate AR, to (3-keto) DHT, can stimulate AR signaling. Biswas, M. G., and Russell, D. W., J Biol Chem. 272, 15959-15966 (1997)). The net effect of this reaction on androgens and Abi metabolism is therefore expected to be concordant and stimulatory because in addition to increasing DHT synthesis, conversion of 3α-OH-5α-Abi to 5α-Abi also increases affinity for AR (FIG. 8D), stimulates androgen-responsive gene expression (FIGS. 8E-G) and tumor growth (FIG. 8H). Our findings that increased conversion of 3α-OH-5α-Abi to 5α-Abi occurs to a greater extent in the LAPC4 model (FIG. 6C) is consistent with the previous identification of preferential oxidation of 5α-androstanediol to DHT also in the LAPC4 model. Mohler et al., Cancer research 71, 1486-1496 (2011). The modest and delayed stimulation of PSA expression by 3α-OH-5α-Abi that we observed in LAPC4 but not LNCaP (FIGS. 8E-G) is also consistent with an indirect effect that is dependent on oxidation to 5α-Abi.

Notwithstanding these considerations, the majority of Abi metabolites found in serum likely form independent of tumor metabolism and result from the activity of hepatic enzymes. Although we found that prostate cancer cell lines readily 5α-reduce D4A, no prostate cancer-dependent 5β-reduction was observed. Both steroid 5α- and 5β-reductase reactions are known to occur in the liver. Nonetheless, in our clinical study adding dutasteride to treatment with Abi acetate, resulted in an approximately 90% decline in circulating concentrations of 5α-Abi, the immediate product of D4A 5α-reduction, with similar declines in the other 5α-Abi metabolites. D4A concentrations concomitantly rose after the addition of dutasteride, supporting the specific pharmacologic effect of dutasteride on D4A metabolism. Numerically, there was also a rise in Abi concentrations and although this did not reach the generally accepted level of statistical significance (P=0.051), it does raise the possibility that SRD5A provides an important mechanism of Abi clearance, at least in a subset of patients.

The effects of dutasteride appeared to lessen slightly at the start of cycle 7 when compared to the start of cycle 3. This might be due to yet undetermined metabolic effects of a longer duration of treatment.

Finasteride, an SRD5A inhibitor structurally related to dutasteride, has been reported to bind and inhibit 5β-reductase. Drury et al., J Biol Chem., 284, 19786-19790 (2009). The absence of any effect on 5β-reduced Abi metabolites demonstrates the remarkable specificity of dutasteride on 5α-reduction of D4A. The presence and maintenance of 5β-reduced metabolites further suggests an "escape" mechanism of metabolism with pharmacologic 5α-reductase inhibition, raising the possibility that D4A, and perhaps Abi concentrations, might be further elevated with 5β-reductase inhibition, resulting in further therapeutic potentiation.

Our studies demonstrate a clear and specific biochemical effect of SRD5A inhibition on D4A metabolism in patients treated with Abi that would be expected to intensify the benefit of Abi therapy. The clinical benefit of fine tuning Abi metabolism with SRD5A inhibition requires further investigation in randomized trials.

EXPERIMENTAL PROCEDURES

Cell lines, drugs and constructs. LNCaP, 293T and VCaP cells were purchased from the American Type Culture Collection (Manassas, Va.) and maintained in RPMI-1640 (LNCaP) or DMEM (293T and VCaP) with 10% FBS (Gemini bio-products). The LAPC4 cell line was kindly provided by Dr. Charles Sawyers (Memorial Sloan Kettering Cancer Center, New York, N.Y.) and grown in Iscove's Modified Dulbecco's Medium with 10% FBS. Stable LAPC4 cell lines with SRD5A1 knockdown were established as previously described. Chang et al., Proc Natl Acad Sci USA., 108, 13728-13733 (2011). Plasmid pcDNA3-c17 (a generous gift of Dr. Walter Miller, University of California, San Francisco, Calif.) was used to establish the 293 stable cell line expressing human CYP17A1 as described. Papari-Zareei et al., Endocrinology 147, 1591-1597 (2006). Cell lines were authenticated by DDC Medical (Fairfield, Ohio) and determined to be *mycoplasma* free with primers. Dutasteride was purchased from Medkoo Biosciences (Chapel Hill, N.C.). Enzalutamide was obtained from Medivation (San Francisco, Calif.). The AKR1C2 expression plasmid was a generous gift of Dr. Trevor Penning (University of Pennsylvania, Philadelphia, Pa.).

Cell Line Metabolism: 0.2 million/ml cells were seeded and incubated in 12-well plates for ~24 h before incubation with the indicated drugs or a mixture of [$^3$H]-labeled (~1,000,000 cpm/well; PerkinElmer, Waltham, Mass.) and non-radioactive androgens (final concentration, 100 nM) at 37° C. Collected medium was treated with β-glucuronidase (*Helix pomatia*; Sigma-Aldrich), extracted with ethyl acetate:isooctane (1:1), and concentrated under nitrogen gas as described. Li et al., 523, 347-351 (2015).

Xenograft Metabolism: $10^7$ VCaP cells with Matrigel were injected subcutaneously into orchiectomized NSG mice with 5 mg, 90 day sustained-release DHEA pellets (Innovative Research of American, Sarasota, Fla.). ~1000 mm$^3$ xenografts were harvested, minced, and cultured in DMEM with 10% FBS at 37° C. with the indicated drugs. Aliquots of medium were collected at the indicated times. Collected medium was processed for HPLC with the same protocol as medium from cell lines.

HPLC

HPLC analysis was performed on a Waters 717 Plus HPLC or an Agilent 1260 HPLC. Dried samples were reconstituted in 50% methanol and separated on Kinetex 100×2.1 mm, 2.6 μm particle size C18 reverse-phase column (Phenomenex, Torrance, Calif.) using a methanol/water gradient at 30° C. The column effluent was analyzed using a 254 nm UV-visible detector or β-RAM model 3 in-line radioactivity detector (IN/US Systems, Inc.) using Liquiscint scintillation cocktail (National Diagnostics, Atlanta, Ga.). All HPLC studies were conducted in triplicate and repeated at least 3 times in independent experiments. Results are shown as mean±SD.

Gene Expression and Immunoblotting

Cells were starved with phenol red-free and serum free-medium for at least 48 h before treatment with the indicated drugs and/or androgens. RNA extraction and cDNA synthesis were performed with the GenElute Mammalian Total RNA miniprep kit (Sigma-Aldrich) and iScript cDNA Synthesis Kit (Bio-Rad, Hercules, Calif.) respectively. Quantitative PCR (qPCR) analysis was conducted in triplicate in an ABI 7500 Real-Time PCR machine (Applied Biosystems) using iTaq Fast SYBR Green Supermix with ROX (Bio-Rad) and primers for TMPRSS2, PSA and RPLPO, as described. Chang et al., Cell 154, 1074-1084 (2013). Accurate quantitation of each mRNA was achieved by normalizing the sample values to RPLPO and to vehicle-treated cells. 50 μg cell lysate was used for immunoblot with rabbit anti-SRD5A1 (Abnova) and mouse anti-β-actin (Sigma-Aldrich) antibodies.

Mouse Xenograft Studies

Male NSG mice, 6 to 8 weeks of age were obtained from the Cleveland Clinic Biological Resources Unit facility. All mouse studies were conducted under a protocol approved by the Cleveland Clinic Institutional Animal Care and Use Committee. $10^7$ VCaP cells were injected subcutaneously with matrigel. Once tumors reached 100 mm$^3$ (length× width×height×0.52), mice were surgically orchiectomized and arbitrarily assigned to vehicle (n=9), 5α-Abi (n=10), or 3α-OH-5α-Abi (n=9) treatment groups. Mice were injected intraperitoneally with 0.15 mL 5α-Abi and 3α-OH-5α-Abi (0.15 mmol/kg/d and 0.075 mmol/kg/d, respectively, in 5% benzyl alcohol and 95% safflower oil solution) every day for up to 20 days. Control groups were administered 0.15 mL 5% benzyl alcohol and 95% safflower oil solution via intraperitoneal injection every day. Tumor volume was measured every other day, and time to increase in tumor volume by 30% was determined (2 sequential increases). Mice were sacrificed at treatment day 20. The significance of the difference between treatment groups was assessed by Kaplan-Meier survival analysis using a log-rank test in SigmaStat 3.5.

AR Competition Assay

Cells were starved with phenol red-free and serum free-medium for at least 48 h and then treated with [$^3$H]-R1881 and the indicated concentrations of drugs for 30 min. Cells were washed thoroughly with PBS and then lysed with RIM buffer. Intracellular radioactivity was measured with a Beckman Coulter LS60001C liquid scintillation counter and normalized to the protein concentration as detected with a Wallac Victor2 1420 Multilabel counter (Perkin Elmer).

Patient Serum Collection and Drug Extraction

Twelve patients with CRPC undergoing treatment with Abi acetate at Cleveland Clinic were consented under an Institutional Review Board—approved protocol (Case 7813). Blood was collected using Vacutainer Plus serum blood collection tubes (#BD367814, Becton Dickenson, Franklin Lakes, N.J.), between 1 and 16 hours after the 1000 mg daily dose of Abi acetate was administered, and allowed to clot. Tubes were centrifuged at 2500 RPM or 1430×g for 10 minutes. Serum aliquots were frozen at −80° C. until processing. To study the effect of dutasteride on Abi metabolism, serum samples were collected from patients treated on a phase II clinical trial at Dana-Farber Cancer Institute (NCT01393730). Each patient received Abi acetate (1,000 mg daily) plus prednisone (5 mg daily) for 2 cycles (8 weeks) and then additional treatment with dutasteride (3.5 mg daily) was initiated. Samples were collected on treatment with Abi alone and after addition of dutasteride (start of cycles 3, 4 and 7). Seventeen patients treated at this institution on this clinical trial had blood available from all 3 time points. One patient had Abi concentrations that were under the limit of detection and was later determine to have stopped treatment because of adverse effects and was therefore not included in the analysis. Drug metabolites and internal standard ($d_4$-abiraterone, Toronto Research Chemicals Inc, Ontario Canada) were extracted from 100 µL of patient serum with methyl tert-butyl ether (Sigma Aldrich, St. Louis, Mo.), evaporated under a stream of nitrogen gas and reconstituted in methanol:water (50:50) prior to mass spectrometry analysis. Standard curves were generated using human serum spiked with known concentrations of each metabolite to enable determination of unknown concentrations in patient samples Mouse Serum Extraction 20 µl of mouse serum were precipitated with 500 µl methanol containing the internal standard ($d_4$-abiraterone) the supernatant was then injected into the mass analyzer. Standard curves were prepared with mice serum spiked with known metabolites concentrations for accurate determination of unknown metabolites concentrations.

Cell Line Media Extraction

200 µl media collected at different time points were extracted with methyl tert-butyl ether (Sigma Aldrich, St. Louis, Mo.), evaporated under a stream of nitrogen gas and reconstituted in methanol:water (50:50) prior to mass spectrometry analysis.

Mass Spectrometry

Samples were analyzed on a ultra high-performance liquid chromatography station (Shimadzu, Kyoto, Japan) with a DGU-20A3R degasser, 2 LC-30AD pumps, a SIL-30AC autosampler, a CTO-10A column oven and a CBM-20A system controller in tandem with a QTRAP 5500 mass spectrometer (AB Sciex, Framingham, Mass.). Drug metabolites were ionized using electrospray ionization in positive ion mode. Multiple reaction monitoring was used to follow mass transitions for Abi, IS, and the metabolites (Table 1). Due to the similarity in structure and mass transitions for the metabolites it was necessary to separate them with chromatography. Separation of drug metabolites was achieved using a mobile phase consisting of LC-MS grade (Fisher) methanol: acetonitrile: water:formic acid (39: 26:34:1) at a flow rate of 0.2 ml/min., and C18 analytical column; Zorbax Eclipse plus 150×2.1 mm, 3.5 µm (Agilent, Santa Clara, Calif.).

TABLE 1

Parent ion (Q1) and product ion (Q3) for Abi metabolites and the IS

| Analyte | Q1 (m/z) | Q3 (m/z) |
|---|---|---|
| Abiraterone | 350.5 | 156.1 |
| D4A | 348.3 | 156.1 |
| 3-keto-5α-abi | 350.3 | 156.2 |
| 3-keto-5β-abi | 350.4 | 156.1 |
| 3α-OH-5α-abi | 352.4 | 156.2 |
| 3α-OH-5β-abi | 352.4 | 156.4 |
| 3β-OH-5α-abi | 352.3 | 156.1 |
| 3β-OH-5β-abi | 352.1 | 156.1 |
| d4-Abiraterone (IS) | 354.4 | 160.1 |

Example 3: Synthesis for Abiraterone (Abi) Metabolites

Chemical Synthesis

We have developed synthesis for abiraterone (Abi) metabolites: D4A, 5α-Abi, 3α-hydroxy-5α-Abi, 3β-hydroxy-5α-Abi, 5β-Abi, 3α-hydroxy-5β-Abi and 3β-hydroxy-5β-Abi. The synthesis of 3β-hydroxy-5α-Abi started with 3β-hydroxy-5α-androstan-17-one, protecting the hydroxyl group as the acetate, and forming the 16,17-enol triflate, which was treated with 3-diethylpyridyl borane in a Suzuki coupling reaction (yield ~85% Scheme 1). The acetyl group was removed by solvolysis in potassium hydroxide to afford 3β-hydroxy-5α-Abi, and this compound was oxidized with chromic acid to afford 5α-Abi (yield ~90%). The 3α-hydroxy-5α-Abi was prepared from 3β-hydroxy-5α-Abi by inverting the stereochemistry at C-3 via Mitsunobu reaction. The rationale for this approach is that the starting material 3β-hydroxy-5α-androstan-17-one is much cheaper than 3α-hydroxy-5α-androstan-17-one yet yields all 3 compounds; hence, the developed synthesis is very economical. The corresponding 5β-analogs were synthesized with the same strategy starting from etiocholanolone (3α-hydroxy-5β-androstan-17-one), but the yield for Mitsunobu reaction was lower for synthesis of 3β-hydroxy-5β-Abi (Scheme-2). The synthesis of D4A started with DHEA using same procedure as earlier, except using Oppenauer oxidation to convert 3β-hydroxy-$\Delta^5$-Abi to D4A, in overall improved yield for both coupling and Oppenauer reactions (Scheme 3).

Scheme 1: 5α-Abi, 3α-hydroxy-5α-Abi, 3β-hydroxy-5α-Abi

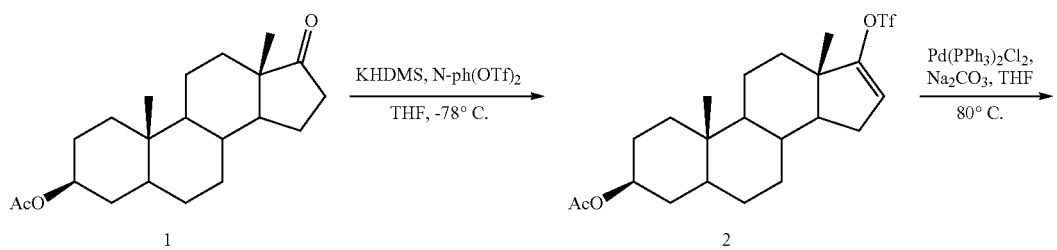

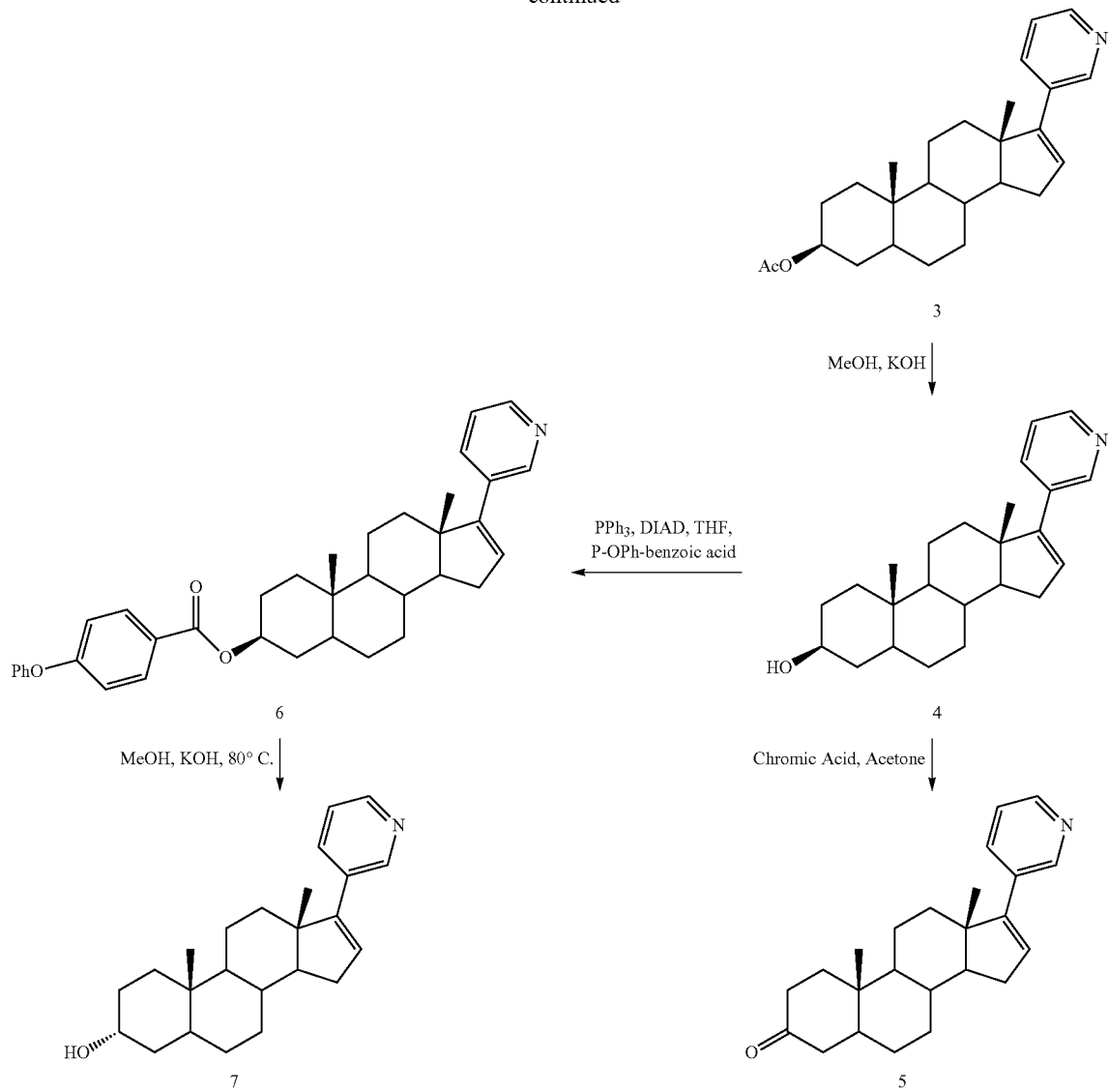

General Procedure for C-3 Acetyl Protection Formation:

To the starting material dissolved in pyridine was added acetic anhydride, and the reaction was stirred at room temperature for 6-7 h. On completion, the reaction was poured onto ice-cold water with vigorous stirring for one hour. The white precipitate formed was filtered and washed with an excess of water and dried under vacuum overnight.

3β-Acetoxy-5α-androsta-16-ene-17-yl-trifluoromethanesulfonate (2)

A solution of compound 1 (1.63 g, 4.9 mmol) in tetrahydrofuran (20 mL) at −78° C. was treated with potassium bis(trimethylsilyl)amide (KHMDS, 0.5 M, 9.8 mL, 4.9 mmol) and stirred for 1 h at −78° C. N-phenyl-bis(triflouromethanesulfonamide) (2.09 g, 5.88 mmol) was added, and the reaction was stirred at −78° C. for 2 h, then slowly warmed to room temperature and quenched with saturated NH$_4$Cl. The product was extracted with ethyl acetate, and the organic phase was washed with water, dried over Na$_2$SO$_4$, and concentrated under reduced pressure. Compound 2 was purified by flash column chromatography on silica gel (hexanes to 10% ethyl acetate in hexanes), yield: 85%. $^1$H NMR (400 MHz, CDCl$_3$) δ: 5.5 (s, 1H), 4.7 (s, 1H), 1.9 (s, 3H), 0.9 (s, 3H), 0.7 (s, 3H) ppm.

3β-Acetoxy-17-(3-pyridyl)-5α-androsta-16-ene (3)

A suspension of compound 2 (2 g, 4.30 mmol), diethyl-3-pyridylborane (758.5 mg, 5.48 mmol), bis(triphenylphosphine)palladium (II) chloride (30 mg, 0.043 mmol) in THF (20 mL) was added to an aqueous solution of sodium carbonate (2 M, 7.5 mL). The mixture was refluxed for 18 h under N$_2$. The reaction was concentrated under reduced pressure, and the residue was extracted with ethyl acetate; the organic phase was washed with brine, dried over Na$_2$SO$_4$ and concentrated under reduced pressure. Compound 3 was purified by flash column chromatography on silica gel (hexanes to 50% ethyl acetate in hexanes), yield: 90%. $^1$H NMR (400 MHz, CDCl$_3$) δ: 8.6 (s, 1H), 8.5 (d, J=4.8 Hz, 1H), 7.7 (d, J=7.6 Hz, 1H), 7.3 (dd, J1=4.8 Hz and J2=7.6 Hz, 1H), 6.0 (s, 1H), 4.7 (bs, 1H), 2.24 (d, 1H), 2.0-0.9 (m, 16H), 1.0 (s, 3H), 0.98 (s, 3H) ppm. $^{13}$C NMR (100 MHz, CDCl$_3$) δ: 170.6, 151.7, 147.8, 143.7, 140.8, 133.6, 129.1, 122.9, 69.9, 21.5, 11.3, 9.1 ppm.

17-(3-pyridyl)-5α-androsta-16-ene-3β-ol (3β-hydroxy-5α-Abi; 4)

Compound 3 (800 mg, 1.2 mmol) was dissolved in methanol (10 mL) at room temperature. A solution of 10% KOH in methanol (7 mL) was added, and the mixture was stirred for 1.5 h, then concentrated under reduced pressure. Dichloromethane (40 mL) and water (40 mL) were added, and the mixture was stirred for 1 h. The organic phase was separated and dried over Na$_2$SO$_4$. Compound 4 was purified by flash column chromatography on silica gel (hexanes to 50% ethyl acetate in hexanes), yield: 85%, purity 99.3% by HPLC. $^1$H NMR (400 MHz, CDCl$_3$) δ: 8.6 (s, 1H), 8.4 (d, J=4.8, 1H), 7.6 (d, J=7.6, 1H), 7.2 (dd, J$_1$=4.8 Hz and J$_2$=7.6 Hz, 1H), 5.9 (d, J=1.6 Hz), 3.6 (m, 1H), 2.2 (d, 1H), 2.0 (t, 2H), 1.2-1.8 (m, 17H), 0.9 (s, 3H), 0.8 (s, 3H) ppm. $^{13}$C NMR (100 MHz, CDCl$_3$) δ: 151.5, 147.4, 147.3, 133.9, 133.1, 129.3, 123.1, 66.3, 57.5, 54.5, 47.5, 39.3, 36.2, 35.3, 34.0, 31.8, 31.7, 29.0, 28.4, 20.7, 16.7, 11.2 ppm. HRMS measured m/z for [M+H]=352.2642 and predicted m/z=352.2635.

17-(3-pyridyl)-5α-androsta-16-ene-3-one (5α-Abi; 5)

To a solution of compound 4 (270 mg, 0.14 mmol) in acetone (25 mL), 10% (w/v) chromic acid (4.5 mL) was added drop-wise at 0° C. The mixture was stirred at room temperature for 3 h, and a solution of sodium bicarbonate was then added to a pH=7. The reaction mixture was extracted with ethyl acetate, and the organic phase was washed with water and dried over Na$_2$SO$_4$. Compound 5 was purified by flash column chromatography on silica gel (hexanes to 40% ethyl acetate in hexanes), yield: 85%, purity 99.4% by HPLC. $^1$H NMR (400 MHz, CDCl$_3$) δ: 8.6 (s, 1H), 8.4 (d, J=4.8, 1H), 7.6 (d, J=7.6, 1H), 7.2 (dd, J$_1$=4.8 Hz and J$_2$=7.6 Hz, 1H), 5.9 (d, J=1.6 Hz), 2.4-1.2 (m, 20H), 1.1 (s, 3H), 1.0 (s, 3H) ppm. $^{13}$C NMR (100 MHz, CDCl$_3$) δ: 211.8, 151.5, 147.4, 147.3, 134.2, 133.1, 129.3, 123.1, 66.3, 57.5, 54.5, 47.5, 39.3, 36.2, 35.3, 34.0, 31.8, 31.7, 29.0, 28.4, 20.7, 16.7, 11.2 ppm. HRMS measured m/z for [M+H]= 350.2489 and predicted m/z=350.2478.

17-(3-pyridyl)-5α-androsta-16-ene-3α-(4-phenoxy)benzoate (6)

Compound 4 (132 mg, 0.375 mmol), triphenyl phosphine (108 mg, 0.412 mmol) and 4-phenoxybenzoic acid (81 mg, 0.375 mmol) were dissolved in dry THF (5 mL) and cooled to 0° C. for 15 minutes before adding diisopropylazodicarboxylate slowly, allowing the yellow color to disappear between the additions. The mixture was stirred for 2.5 h, and the volatile components were removed under reduced pressure. Compound 6 was purified from the residue by flash column chromatography on silica gel (20% ethyl acetate in hexanes as eluent), yield: 85%. $^1$H NMR (400 MHz, CDCl$_3$) δ: 8.6 (s, 1H), 8.4 (d, J=4.8, 1H), 8.0 (d, 2H), 7.6 (d, J=7.6, 1H), 7.35 (t, 2H), 7.2 (dd, J$_1$=4.8 Hz and J$_2$=7.6 Hz, 1H), 7.16 (dd, 1H), 7.03 (d, 2H), 6.97 (d, 2H), 5.94 (d, J=1.6 Hz), 5.25 (bs, 1H), 2.2 (d, 1H), 2.0 (t, 2H), 1.2-1.8 (m, 17H), 0.97 (s, 3H), 0.96 (s, 3H) ppm.

17-(3-pyridyl)-5α-androsta-16-ene-3α-ol (3α-hydroxy-5α-Abi; 7)

Compound 6 (40 mg, 0.102 mmol) was dissolved in methanol (4 mL) at room temperature. A solution of 10% KOH in methanol (2.0 mL) was added, and the mixture was stirred for 2-3 h at 80° C. and then concentrated under reduced pressure. Dichloromethane (25 mL) and water (25 mL) were added, and the mixture was stirred for 1 h. The organic phase was separated and dried over Na$_2$SO$_4$. Compound 7 was purified by flash column chromatography on silica gel (hexanes to 50% ethyl acetate in hexanes), yield: 85%. $^1$H NMR (400 MHz, CDCl$_3$) δ: 8.6 (s, 1H), 8.4 (d, J=4.8, 1H), 7.6 (d, J=7.6, 1H), 7.2 (dd, J$_1$=4.8 Hz and J$_2$=7.6 Hz, 1H), 5.9 (d, J=1.6 Hz), 4.1 (m, 1H), 2.2 (d, 1H), 2.0 (t, 2H), 1.2-1.8 (m, 17H), 0.9 (s, 3H), 0.8 (s, 3H) ppm. $^{13}$C NMR (100 MHz, CDCl$_3$) δ: 151.5, 147.4, 147.3, 133.9, 133.1, 129.3, 123.1, 66.3, 57.5, 54.5, 47.5, 39.3, 36.2, 35.3, 34.0, 31.8, 31.7, 29.0, 28.4, 20.7, 16.7, 11.2 ppm. HRMS measured m/z for [M+H]=352.2642 and predicted m/z=352.2635.

Scheme 2: Synthesis of 5β-Abi, 3α-hydroxy-5β-Abi and 3β-hydroxy-5β-Abi

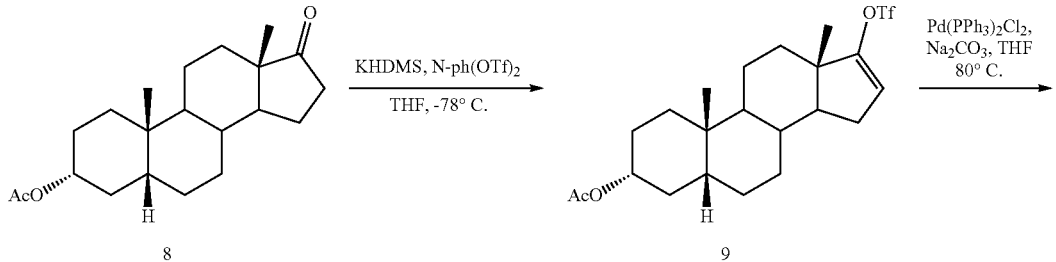

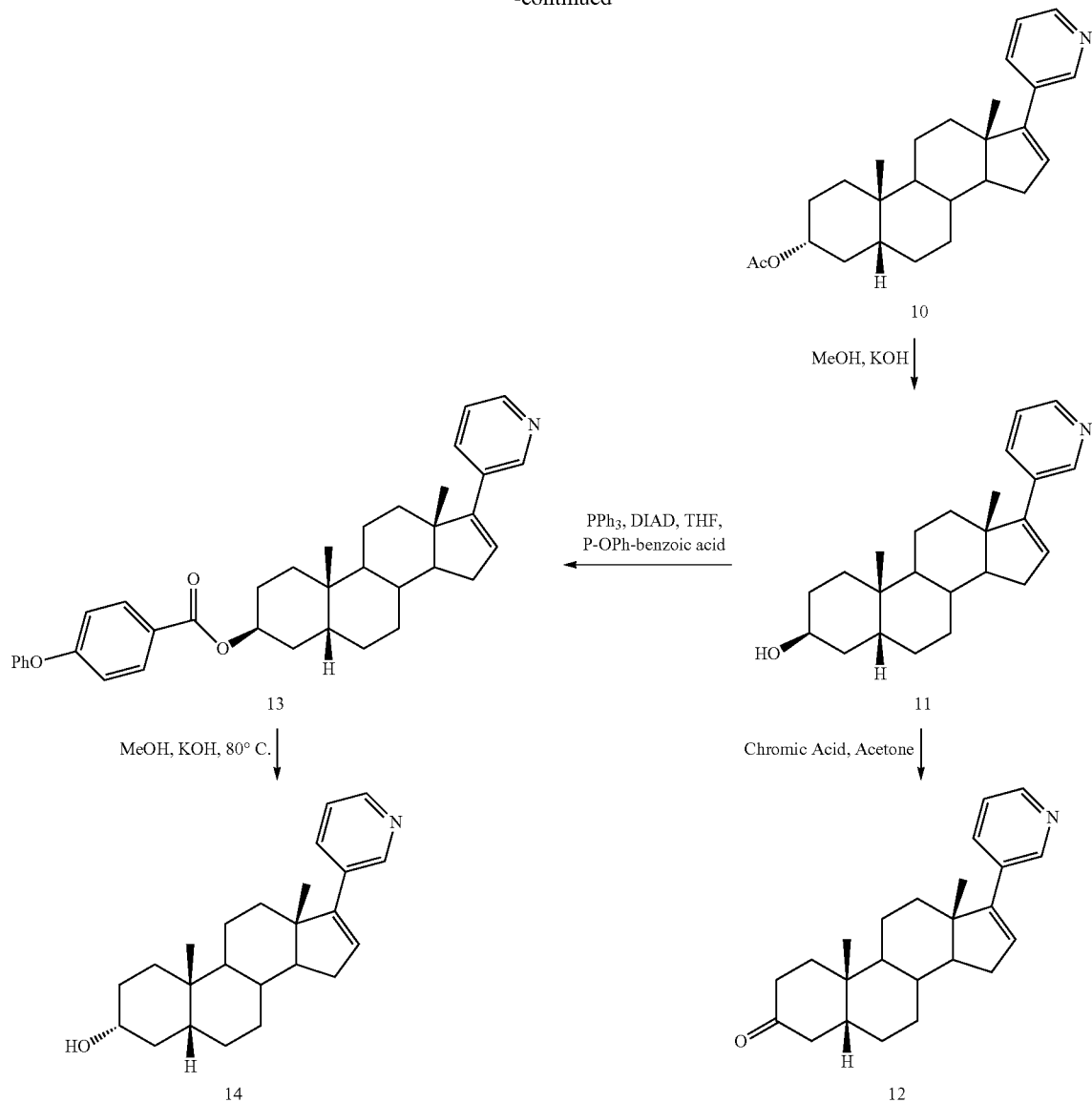

3α-Acetoxy-5β-androsta-16-ene-17-yl-trifluoromethanesulfonate (9)

A solution of compound 8 (500 mg, 1.50 mmol) in tetrahydrofuran (6 mL) at −78° C. was treated with potassium bis(trimethylsilyl)amide (KHMDS, 0.7 M, 2.4 mL, 1.50 mmol) and stirred for 1 h at −78° C. N-phenyl-bis(triflouromethanesulfonamide) (626 mg, 1.81 mmol), was added, and the reaction was stirred at −78° C. for 2 h, then slowly warmed to room temperature and quenched with saturated $NH_4Cl$. The product was extracted with ethyl acetate, and the organic phase was washed with water, dried over $Na_2SO_4$, and concentrated under reduced pressure. Compound 9 was purified by flash column chromatography on silica gel (hexanes to 10% ethyl acetate in hexanes), yield: 85%. $^1$H NMR (400 MHz, $CDCl_3$) δ: 4.70 (s, 1H), 2.02 (s, 3H), 0.94 (s, 3H), 0.93 (s, 3H) ppm.

3α-Acetoxy-17-(3-pyridyl)-5β-androsta-16-ene (10)

A suspension of compound 9 (698 mg, 1.50 mmol), diethyl-3-pyridylborane (265 mg, 1.80 mmol), bis(triphenylphosphine)palladium (II) chloride (11.0 mg, 0.015 mmol) in THF (15 mL) was added to an aqueous solution of sodium carbonate (2 M, 5 mL). The mixture was refluxed for 18 h under $N_2$. The reaction was concentrated under reduced pressure, and the residue was extracted with ethyl acetate. The organic phase was washed with brine, dried over $Na_2SO_4$, and concentrated under reduced pressure. Compound 10 was purified by flash column chromatography on silica gel (hexanes to 50% ethyl acetate in hexanes), yield: 90%. $^1$H NMR (400 MHz, $CDCl_3$) δ: 8.6 (s, 1H), 8.5 (d, J=4.8 Hz, 1H), 7.7 (d, J=7.6 Hz, 1H), 7.3 (dd, J1=4.8 Hz and J2=7.6 Hz, 1H), 6.0 (s, 1H), 4.75 (bs, 1H), 2.24 (d, 1H), 2.0-0.9 (m, 16H), 1.0 (s, 3H), 0.98 (s, 3H) ppm.

17-(3-pyridyl)-5β-androsta-16-ene-3α-ol (3α-hydroxy-5β-Abi; 11)

Compound 10 (150 mg, 0.383 mmol) was dissolved in methanol (5 mL) at room temperature. A solution of 10% KOH in methanol (2.0 mL) was added, and the mixture was stirred for 1.5 h and then concentrated under reduced pressure. Dichloromethane (25 mL) and water (25 mL) were added, and the mixture was stirred for 1 h. The organic phase was separated and dried over $Na_2SO_4$. Compound 11 was purified on florisil column chromatography (hexanes to 50% ethyl acetate in hexanes), yield: 35%. $^1$H NMR (400 MHz, $CDCl_3$) δ: 8.6 (s, 1H), 8.4 (d, J=4.8, 1H), 7.6 (d, J=7.6, 1H), 7.2 (dd, $J_1$=4.8 Hz and $J_2$=7.6 Hz, 1H), 5.9 (d, J=1.6 Hz), 3.6 (m, 1H), 2.2 (d, 1H), 2.0 (t, 2H), 1.2-1.8 (m, 17H), 0.97 (s, 3H), 0.96 (s, 3H) ppm.

17-(3-pyridyl)-5β-androsta-16-ene-3-one (5β-Abi; 12)

To a solution of compound 11 (50 mg, 0.14 mmol) in acetone (4 mL), 10% (w/v) chromic acid (1.0 mL) was added drop-wise at 0° C. The mixture was stirred at room temperature for 3 h, and a solution of sodium bicarbonate was then added to a pH=7. The reaction mixture was extracted with ethyl acetate, and the organic phase was washed with water and dried over $Na_2SO_4$. Compound 12 was purified by flash column chromatography on silica gel (hexanes to 40% ethyl acetate in hexanes), yield: 85%, purity 99.4% by HPLC. $^1$H NMR (400 MHz, $CDCl_3$) δ: 8.6 (s, 1H), 8.4 (d, J=4.8, 1H), 7.6 (d, J=7.6, 1H), 7.2 (dd, $J_1$=4.8 Hz and $J_2$=7.6 Hz, 1H), 5.9 (d, J=1.6 Hz), 2.4-1.2 (m, 20H), 1.1 (s, 3H), 1.0 (s, 3H) ppm.

17-(3-pyridyl)-5β-androsta-16-ene-3β-(4-phenoxy)benzoate (13)

Compound 11 (132 mg, 0.375 mmol), triphenyl phosphine (108 mg, 0.412 mmol) and 4-phenoxybenzoic acid (81 mg, 0.375 mmol) were dissolved in dry THF (5 mL) and cooled to 0° C. for 15 minutes before adding diisopropylazodicarboxylate slowly, allowing the yellow color to disappear between additions. The mixture was stirred for 2.5 h, and the volatile components were removed under reduced pressure. Compound 13 was purified from the residue by flash column chromatography on silica gel (20% ethylacetate in hexanes as eluent), yield: 35%. $^1$H NMR (400 MHz, $CDCl_3$) δ: 8.6 (s, 1H), 8.4 (d, J=4.8, 1H), 8.0 (d, 2H), 7.6 (d, J=7.6, 1H), 7.35 (t, 2H), 7.2 (dd, $J_1$=4.8 Hz and $J_2$=7.6 Hz, 1H), 7.16 (dd, 1H), 7.03 (d, 2H), 6.97 (d, 2H), 5.94 (d, J=1.6 Hz), 5.25 (bs, 1H), 2.2 (d, 1H), 2.0 (t, 2H), 1.2-1.8 (m, 17H), 0.97 (s, 3H), 0.96 (s, 3H) ppm.

17-(3-pyridyl)-5β-androsta-16-ene-3β-ol (3β-hydroxy-5β-Abi; 14)

Compound 13 (40 mg, 0.102 mmol) was dissolved in methanol (4 mL) at room temperature. A solution of 10% KOH in methanol (2.0 mL) was added, and the mixture was stirred for 2-3 h at 80° C., then concentrated under reduced pressure. Dichloromethane (25 mL) and water (25 mL) were added, and the mixture was stirred for 1 h. The organic phase was separated and dried over $Na_2SO_4$. Compound 14 was purified by flash column chromatography on silica gel (hexanes to 50% ethyl acetate in hexanes), yield: 85%. $^1$H NMR (400 MHz, $CDCl_3$) δ: 8.6 (s, 1H), 8.4 (d, J=4.8, 1H), 7.6 (d, J=7.6, 1H), 7.2 (dd, $J_1$=4.8 Hz and $J_2$=7.6 Hz, 1H), 5.9 (d, J=1.6 Hz), 4.1 (m, 1H), 2.2 (d, 1H), 2.0 (t, 2H), 1.2-1.8 (m, 17H), 0.97 (s, 3H), 0.96 (s, 3H) ppm.

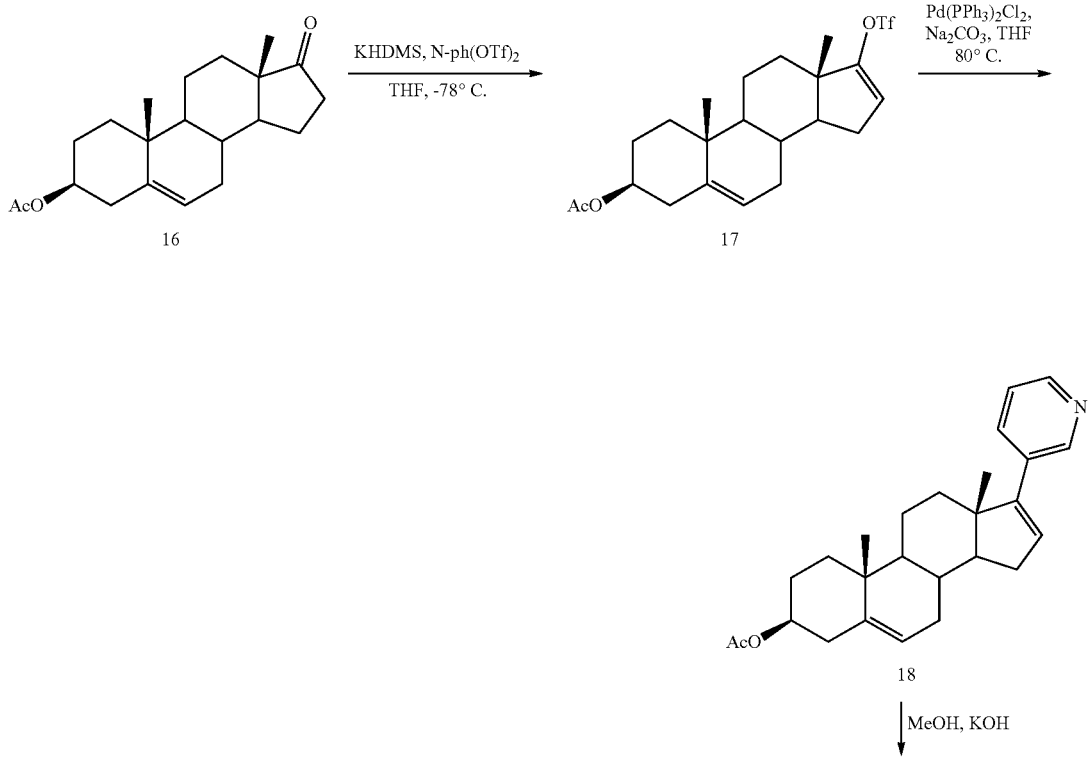

Scheme 3: Synthesis of D4A

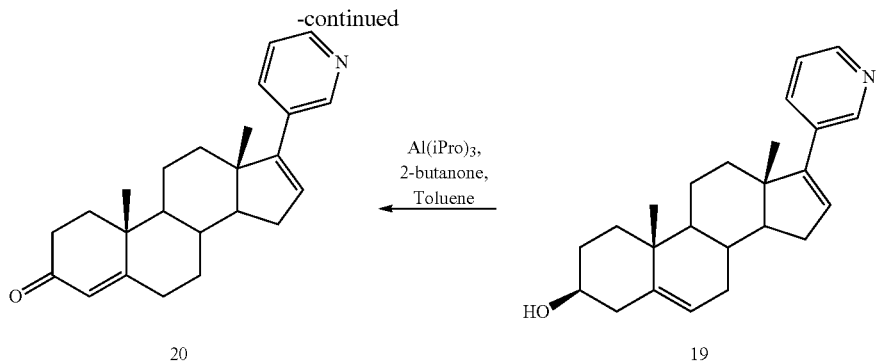

3β-Acetoxy-5α-androsta-16-ene-17-yl-trifluoromethanesulfonate (17)

A solution of 16 (4.0 g, 12.10 mmol) in tetrahydrofuran at −78° C. was treated with potassium hexamethyldisilazane (KHMDS, 0.5 M, 24.0 mL, 12.10 mmol) and stirred for 1 hour at −78° C. N-phenyl-bis(triflouromethanesulfonimide) (5.18 g, 14.52 mmol), was added, and the reaction was stirred at −78° C. for 2 hours, then warmed slowly to room temperature and quenched with saturated NH$_4$Cl. After concentration under reduced pressure, and the residue was extracted with ethyl acetate, and the organic phase was washed with brine, dried with Na$_2$SO$_4$, and concentrated under reduced pressure. Compound 17 was purified by flash column chromatography on silica gel, yield: 85%. $^1$H NMR (400 MHz, CDCl$_3$) δ: 5.58 (bs, 1H), 5.42-5.32 (m, 1H), 4.66-4.52 (m, 1H), 2.40-2.10 (m, 5H), 2.08-1.40 (m, 18H), 1.24-1.09 (m, 2H), 1.05 (s, 3H), 0.99 (s, 3H) ppm.

3β-Acetoxy-17-(3-pyridyl)-5α-androsta-16-ene (18)

A suspension of compound 17 (3.6 g, 7.78 mmol), diethyl-3-pyridylborane (1.37 g, 9.34 mmol), bis(triphenylphosphine)palladium (II) chloride (54 mg, 0.077 mmol) in THF (35 mL) was added to an aqueous solution of sodium carbonate (2 M, 10 mL). The mixture was refluxed for 18 h under N$_2$. The reaction was concentrated under reduced pressure, and the residue was extracted with ethyl acetate. The organic phase was washed with brine, dried over Na$_2$SO$_4$, and concentrated under reduced pressure. Compound 18 was purified by flash column chromatography on silica gel (hexanes to 50% ethyl acetate in hexanes), yield: 90%. $^1$H NMR (400 MHz, CDCl$_3$) δ: 8.47 (d, J=4 Hz, 1H), 7.68-7.62 (m, 1H), 7.25-7.20 (m, 1H), 5.95 (bs, 1H), 5.48-5.38 (d, 1H, 3.6 Hz), 4.69-4.56 (m, 1H), 2.44-2.22 (m, 4H), 2.16-2.0 (m, 8H), 1.96-1.44 (m, 15H), 1.30-1.00 (m, 11H) ppm. $^{13}$C NMR (100 MHz, CDCl$_3$) δ: 170.82, 151.89, 148.14, 148.08, 140.26, 133.95, 129.49, 123.28, 122.54, 77.52, 77.27, 77.01, 74.10, 57.70, 50.50, 47.56, 38.37, 37.15, 37.01, 35.42, 32.02, 31.73, 30.63, 27.98, 21.70, 21.04, 19.48, 16.82 ppm.

17-(3-pyridyl)-5α-androsta-16-ene-3β-ol (19)

Compound 18 (2.4 g, 3.6 mmol) was dissolved in methanol (30 mL) at room temperature. A solution of 10% KOH in methanol (21 mL) was added, and the mixture was stirred for 1.5 h and then concentrated under reduced pressure. Dichloromethane (80 mL) and water (80 mL) were added, and the mixture was stirred for 1 h. The organic phase was separated and dried over Na$_2$SO$_4$. Compound 19 was purified by flash column chromatography on silica gel (hexanes to 50% ethyl acetate in hexanes), yield: 85%, purity 99.3% by HPLC. $^1$H NMR (400 MHz, CDCl$_3$) δ: 8.6 (s, 1H), 8.4 (d, J=4.8 Hz, 1H), 7.6 (d, J=7.6 Hz, 1H), 7.2 (dd, J$_1$=4.8 Hz and J$_2$=7.6 Hz, 1H), 6.0 (s, 1H), 5.42-5.36 (m, 1H), 3.56-3.42 (m, 1H), 2.48-2.36 (m, 6H), 2.32-1.96 (m 6H), 1.94-1.38 (m, 20H), 1.36-0.86 (m, 16H) ppm. $^{13}$C NMR (100 MHz, CDCl$_3$) δ: 151.91, 148.13, 148.06, 141.37, 133.90, 129.48, 121.59, 71.93, 57.78, 50.58, 47.57, 37.41, 36.93, 35.48, 32.05, 31.86, 31.76, 30.67, 21.11, 19.59, 16.83 ppm.

17-(3-Pyridyl)androsta-4,16-dien-3-one (20)

Toluene (100 mL) was heated to reflux using a Dean-Stark apparatus until 35 mL was distilled off. The remaining toluene (65 mL) was cooled to room temperature, and compound 19 (2.2 g, 6.29 mmol), 2-butanone (20 mL) and aluminium isopropoxide (3.2 g, 15.74 mmol) was added. The reaction was refluxed for an additional 16 hours, and the solvent was then removed under reduced pressure. The product was extracted into ethyl acetate, and the organic phase was washed with brine, dried over Na$_2$SO$_4$, and concentrated under reduced pressure. Compound 20 was purified by flash column chromatography on silica gel (hexanes to 50% ethyl acetate in hexanes), yield: 85%, purity 99.2% by HPLC). $^1$H NMR (400 MHz, CDCl$_3$) δ: 8.6 (s, 1H), 8.4 (d, J=4.8 Hz, 1H), 7.6 (d, J=7.6 Hz, 1H), 7.2 (dd, J$_1$=4.8 Hz and J$_2$=7.6 Hz, 1H), 5.9 (d, J=1.6 Hz), 5.7 (s, 1H), 2.5-1.2 (complex, 16H), 1.2 (s, 3H), 1.0 (s, 3H) ppm. $^{13}$C NMR (100 MHz, CDCl$_3$) δ: 199.3, 170.8, 151.3, 147.5, 147.4, 133.9, 132.8, 129.2, 123.9, 123.1, 56.7, 53.9, 38.6, 35.5, 35.0, 34.1, 33.9, 32.7, 31.7, 31.6, 20.8, 17.2, 16.5 ppm. HRMS measured m/z for [M+H]=348.2328 and predicted m/z=348.2322.

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, while theories may be presented describing possible mechanisms through with the compounds are effective, the inventors are not bound by theories described herein. The invention is not limited to the exact details shown and described, for variations obvious to one skilled in the art will be included within the invention defined by the claims.

The invention claimed is:
1. A method of treating androgen dependent cancers, breast cancer, endometriosis, or adrenal dysfunction in a subject in need thereof, comprising administering a therapeutically effective amount a steroidal CYP17A inhibitor and an effective amount of a 5-α-reductase inhibitor to the subject and modifying treatment by determining the level of one or more steroidal CYP17A inhibitor metabolites in a biological sample from the subject by mass spectrometry, wherein modifying treatment consists of changing the identity, dose, or administration schedule of the 5-α-reductase inhibitor and/or the CYP17A inhibitor, wherein the steroidal CYP17A inhibitor is selected from the group consisting of a $\Delta^5$, 3β-hydroxy steroid and a $\Delta^4$, 3-keto steroid.

2. The method of claim 1, wherein androgen dependent cancer is treated.

3. The method of claim 2, wherein the cancer is prostate cancer.

4. The method of claim 3, wherein the prostate cancer is castration-resistant prostate cancer.

5. The method of claim 1, wherein the steroidal CYP17A inhibitor is selected from the group consisting of abiraterone, the abiraterone metabolite D4A, and galeterone.

6. The method of claim 1, wherein the steroidal CYP17A inhibitor is selected from the group consisting of abiraterone and the abiraterone metabolite D4A.

7. The method of claim 1, wherein the steroidal CYP17A inhibitor is abiraterone, and the steroidal CYP17A inhibitor metabolites are selected from the group consisting of D4A, 3β-OH-5β-abi, 3-keto-5α-abi, 3-keto-5β-abi, 3α-OH-5α-abi, 3α-OH-5β-abi, and 3β-OH-5α-abi.

8. The method of claim 1, wherein the 5-α-reductase inhibitor is selected from the group consisting of dutasteride, finasteride, lapisteride, turosteride, bexlosteride, izonsteride, and epristeride.

9. The method of claim 1, wherein the steroidal CYP17A inhibitor and the 5-α-reductase inhibitor are administered with a pharmaceutically acceptable carrier.

10. The method of claim 1, wherein one or more of the steroidal CYP17A inhibitor and/or the 5-α-reductase inhibitor are administered orally.

11. The method of claim 1, wherein the steroidal CYP17A inhibitor is a $\Delta^5$, 3β-hydroxy steroid.

12. The method of claim 1, wherein the steroidal CYP17A inhibitor is a $\Delta^4$, 3-keto steroid.

* * * * *